(12) United States Patent
Felgner et al.

(10) Patent No.: US 6,433,017 B1
(45) Date of Patent: *Aug. 13, 2002

(54) AMPHIPHILIC POLYAMINE COMPOUNDS

(75) Inventors: Philip L. Felgner, Rancho Santa Fe, CA (US); Xiang Gao, Nashville, TN (US); Jing Ling, Carlsbad, CA (US)

(73) Assignee: Gene Therapy Systems, Inc., San Diego, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 09/796,340

(22) Filed: Feb. 28, 2001

Related U.S. Application Data

(62) Division of application No. 09/448,876, filed on Nov. 24, 1999.
(60) Provisional application No. 60/111,078, filed on Dec. 4, 1998, and provisional application No. 60/110,020, filed on Nov. 25, 1998.

(51) Int. Cl.$^7$ ...................... A61K 31/16; A61K 31/164; A61K 31/165; A61K 31/235; A61K 31/255

(52) U.S. Cl. ........................... 514/616; 514/19; 514/20; 514/533; 514/534; 514/547; 514/604; 514/614; 514/615; 554/91; 554/106; 560/13; 560/34; 560/41; 564/81; 564/82; 564/91; 564/149; 564/151; 564/153

(58) Field of Search ........................... 514/19, 20, 533, 514/534, 547, 604, 614, 615, 616; 560/13, 34, 41; 554/91, 106; 564/81, 82, 91, 149, 151, 153

(56) References Cited

U.S. PATENT DOCUMENTS 5,847,206 A * 12/1998 Pavia et al. .................. 562/575

* cited by examiner

Primary Examiner—Peter O'Sullivan
(74) Attorney, Agent, or Firm—Stephen E. Reiter; Foley & Lardner

(57) ABSTRACT

In accordance with the present invention, there are provided amphiphilic polyamine compounds and derivatives thereof having the property of promoting transfection of polynucleotides and polypeptides into cells, and formulations comprising said compounds.

49 Claims, 36 Drawing Sheets

Old XG40 Batch

New XG40 Batch

B16-F0 Cells

COS.7 Cells

BHK-21 Cells

HeLa-S3 Cells

Jurkat Cells

PC 12 Cells

COS.1 Cells

NIH-3T3 Cells

CHO Cells

293 Cells

CV 1 Cells

Synthetic scheme for 18-1-lys 5Tε
Step 1: synthesis of 18-1
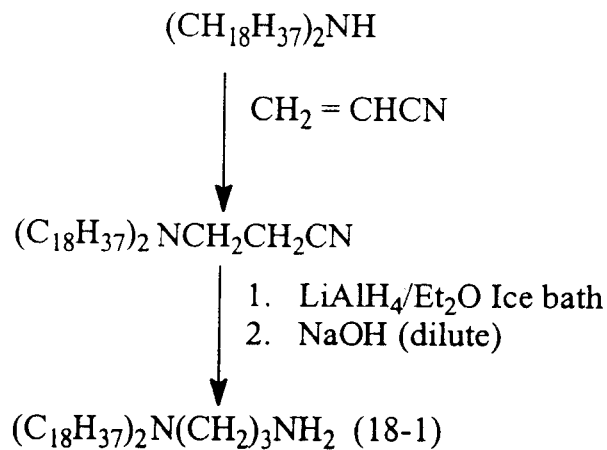
Step 2: synthesis of 18-1-lys-1
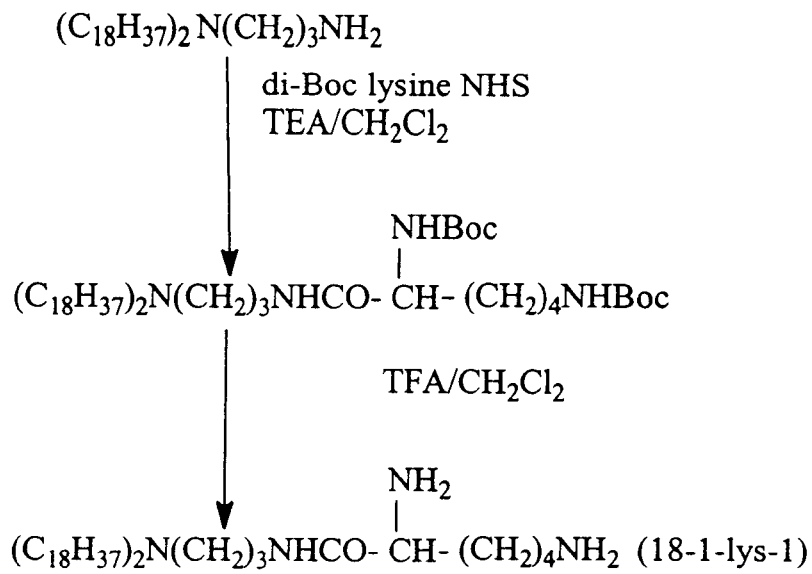
Fig. 9A Step 3: synthesis of 18-1-lys 3

Step 4: synthesis of 18-1-lys 5Tε
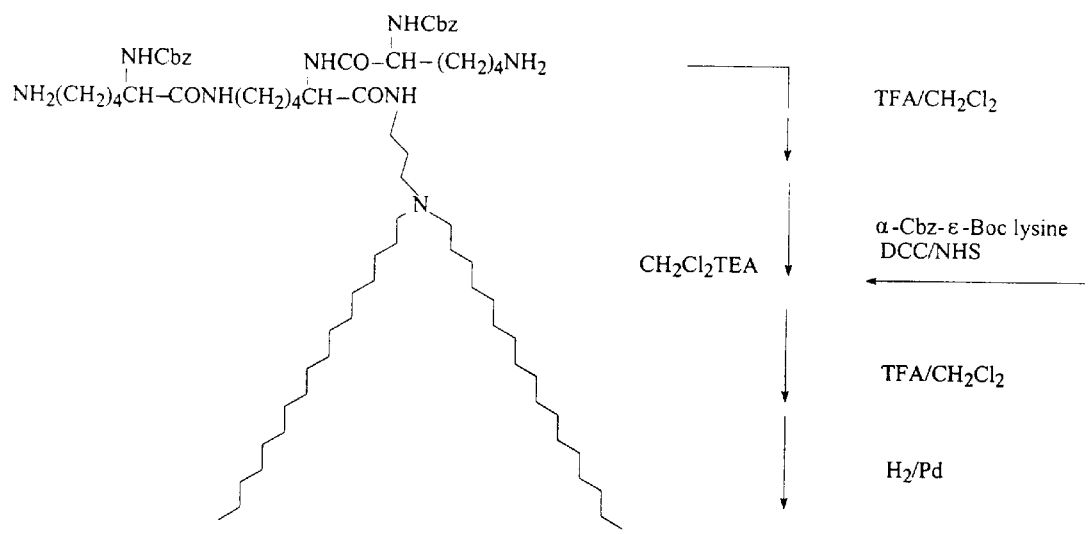
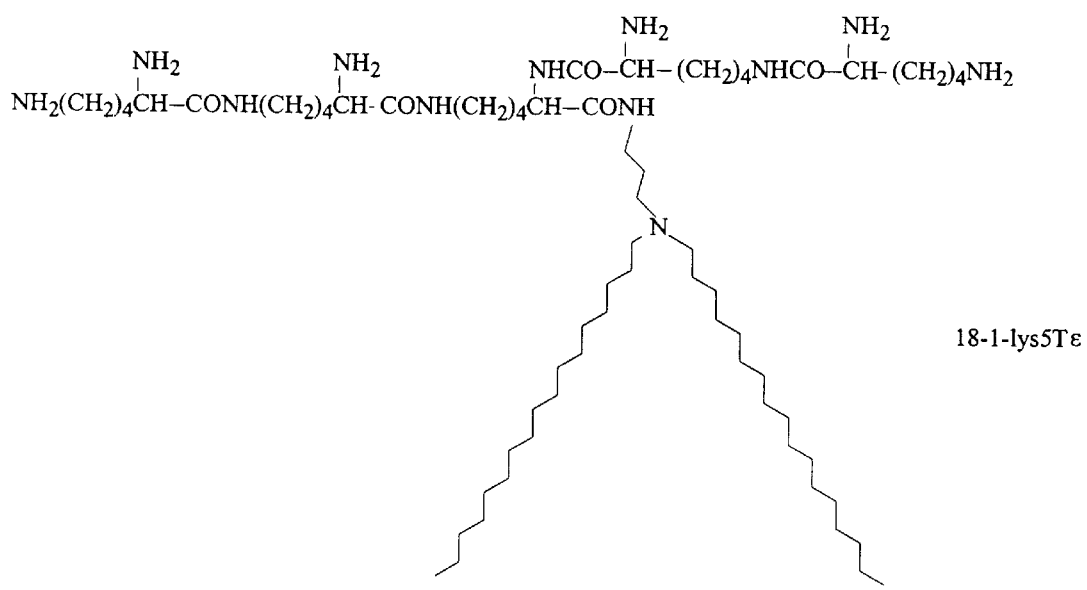
Fig. 9C

A. Synthesis of 18-1-lys 5Tε analogues with different fatty chains

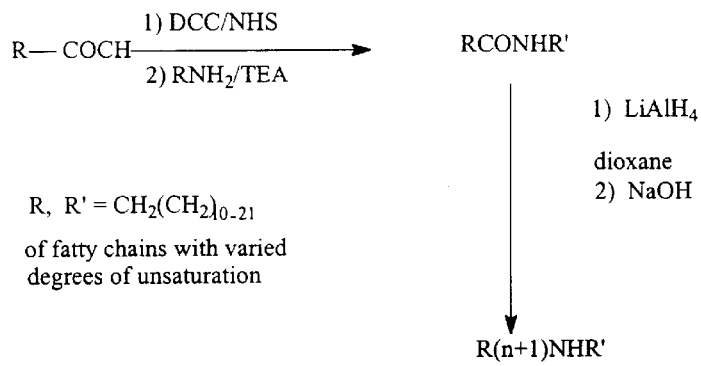

R, R' = $CH_2(CH_2)_{0-21}$
of fatty chains with varied
degrees of unsaturation

B. Synthesis of 18-1-lys 5Tε analogues with different lysine groups

| Compounds | protected lysine | structural feature | type and numer of functional groups |
|---|---|---|---|
| 18-1-lys 5Tε | ε-boc α-CBZlysine | T-shape | 4 α-$NH_2$, 1ε-$NH_2$ |
| 18-1-lys 5Tα | α-boc ε-CBZlysine | T-shape | 2 α-$NH_2$, 4ε-$NH_2$ |
| 18-1-lys 5Lε | ε-boc α-CBZlysine | linear | 4 α-$NH_2$, 1ε-$NH_2$ |
| 18-1-lys 5Lα | α-boc ε-CBZlysine | linear | 1 α-$NH_2$, 5ε-$NH_2$ |
| 18-1-lys 7D | α-boc lysine | Dendridic | 4 α-$NH_2$, 4ε-$NH_2$ |

Fig. 10

FIG. 11A
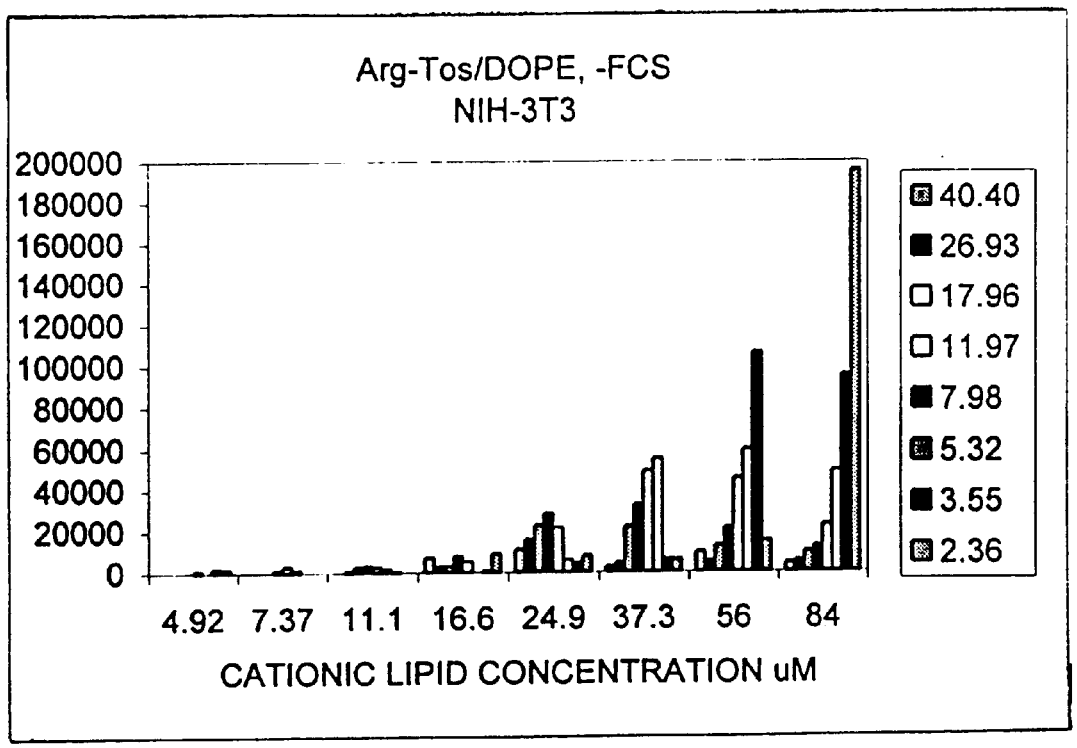
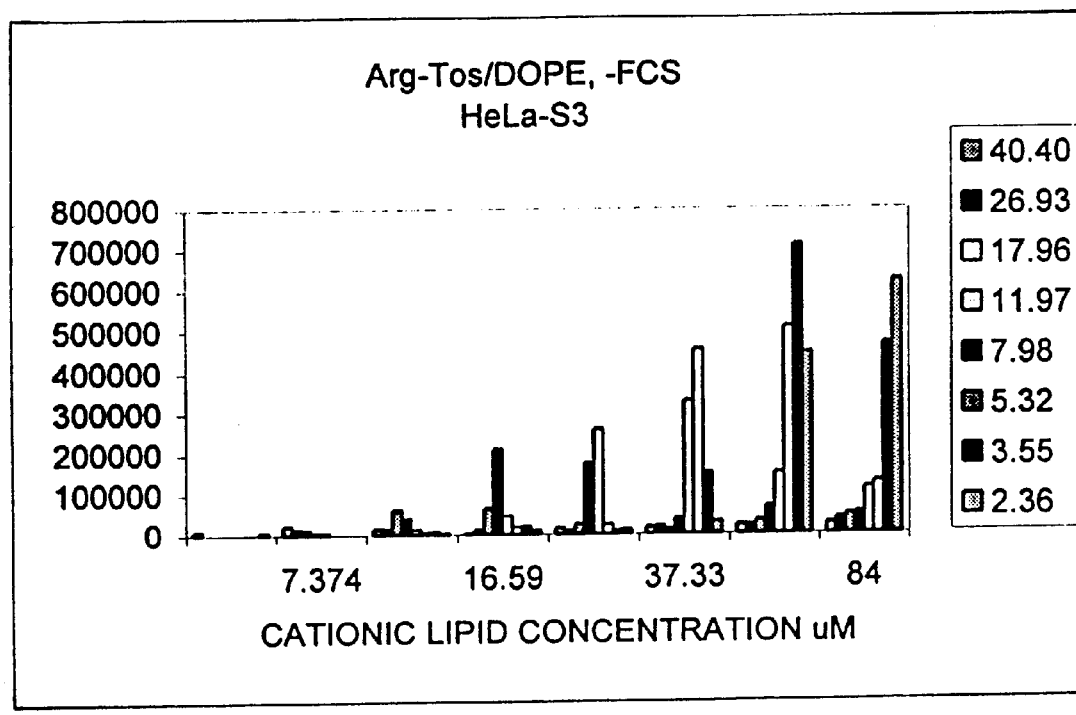
FIG. 11B

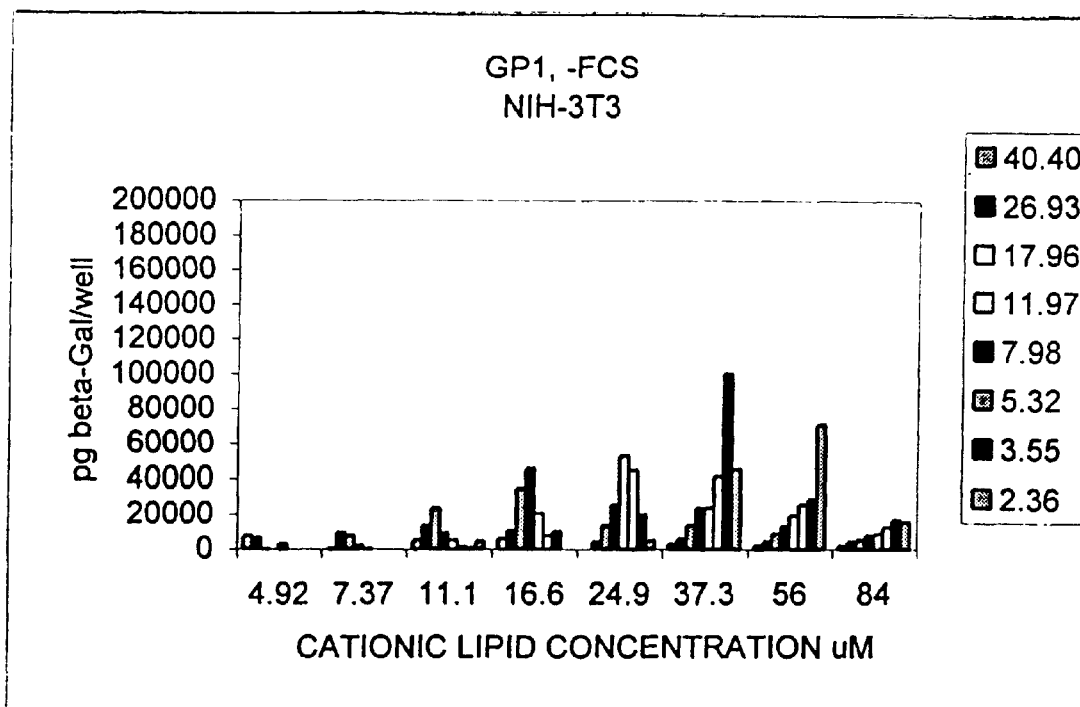
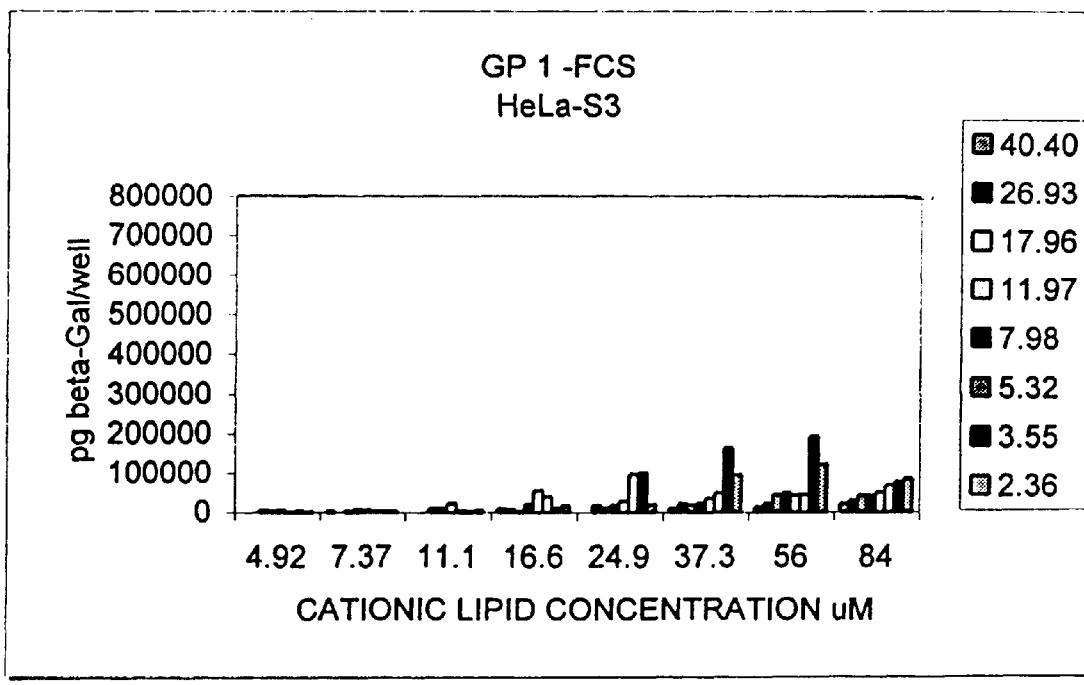

FIG. 12C
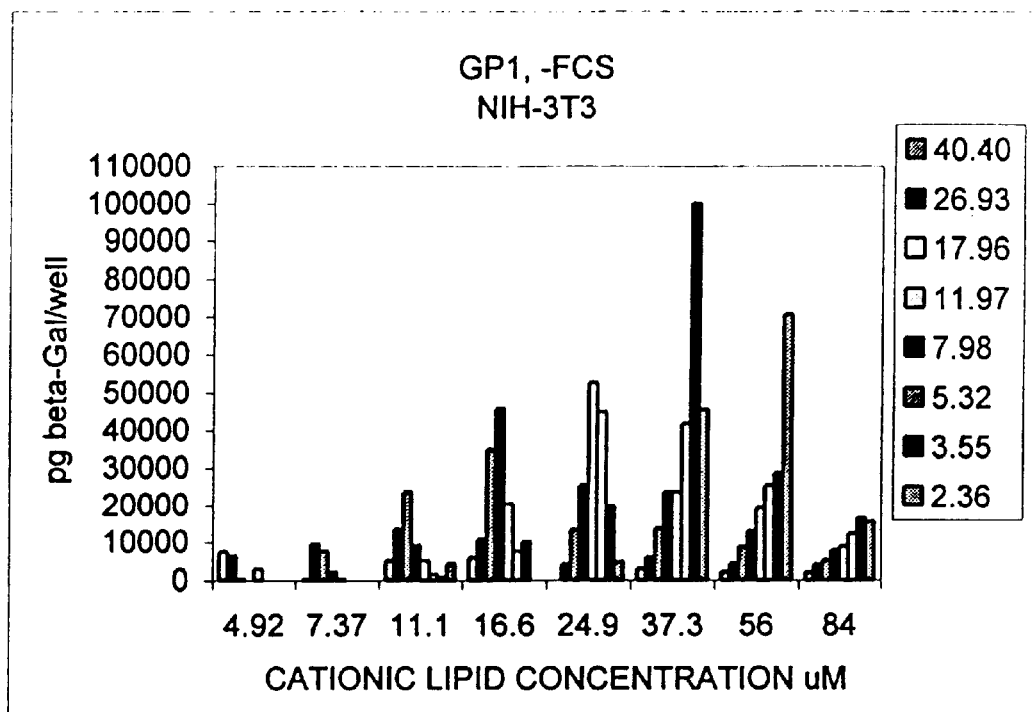
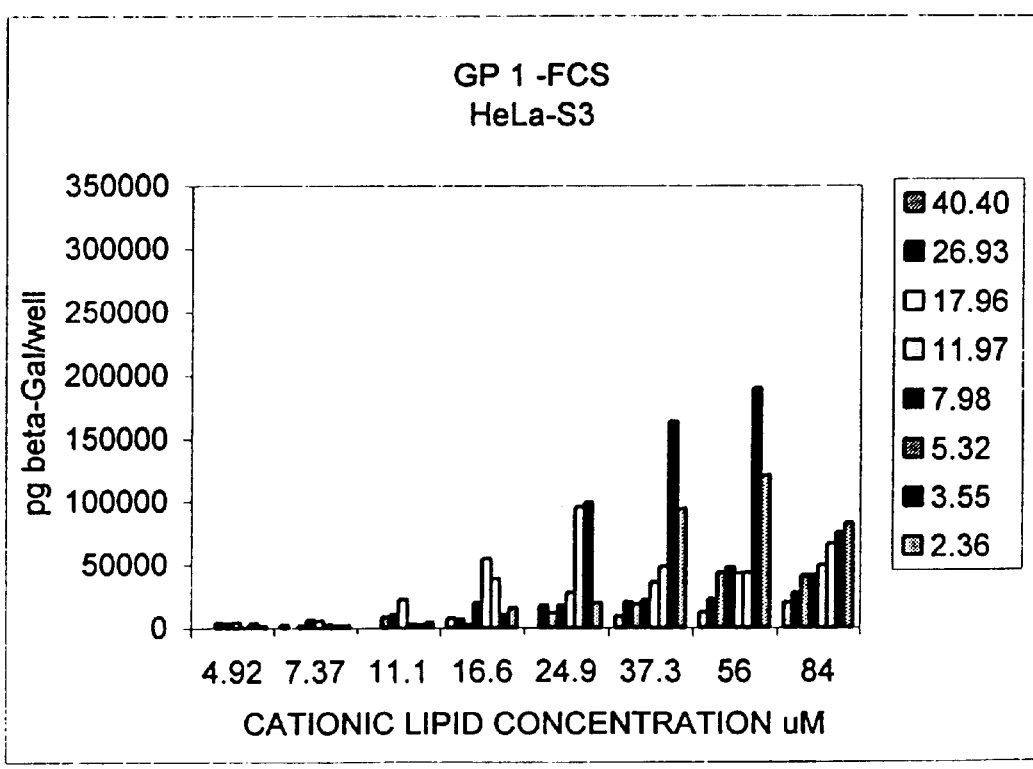
FIG. 12D

FIG. 13C
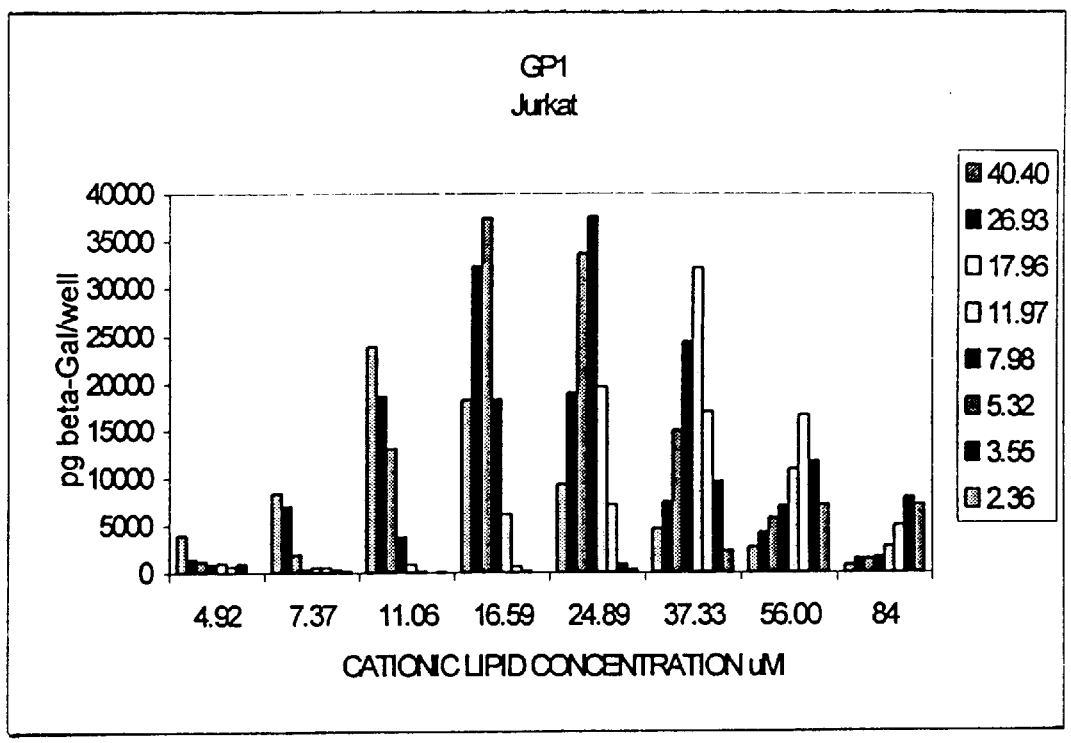
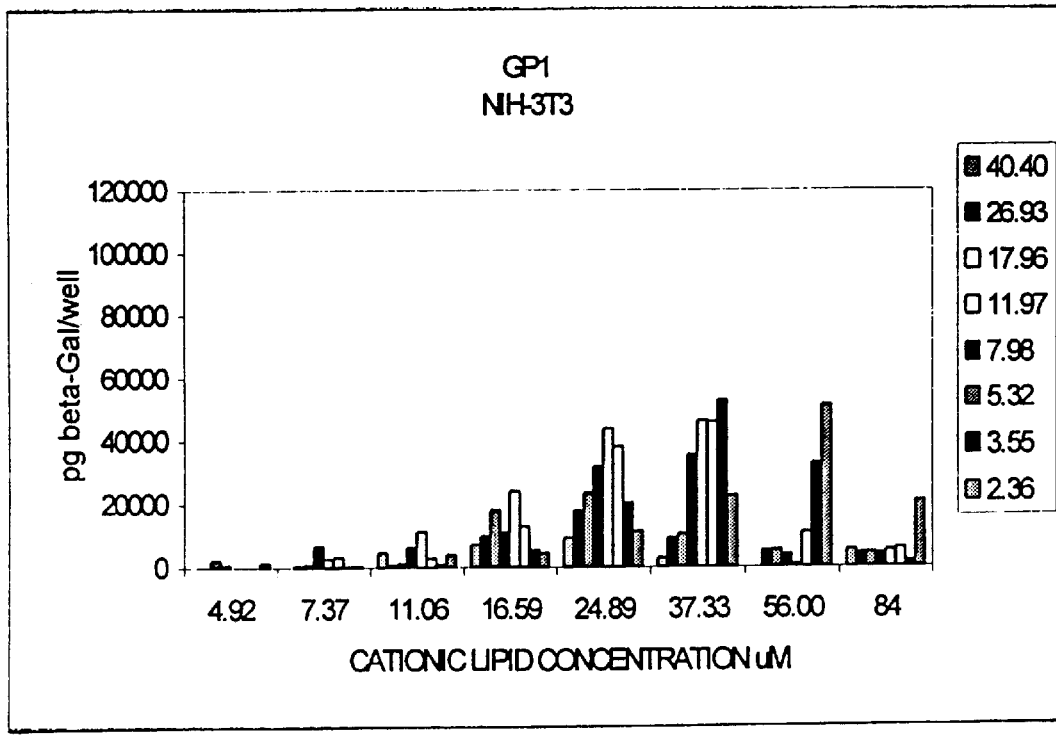
FIG. 13D

FIG. 14A
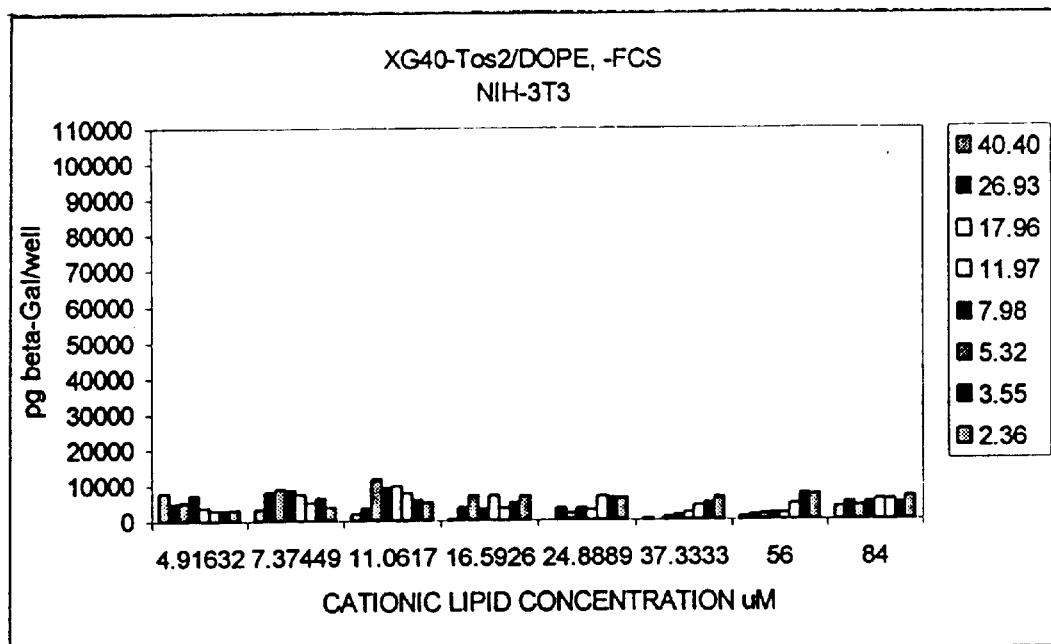
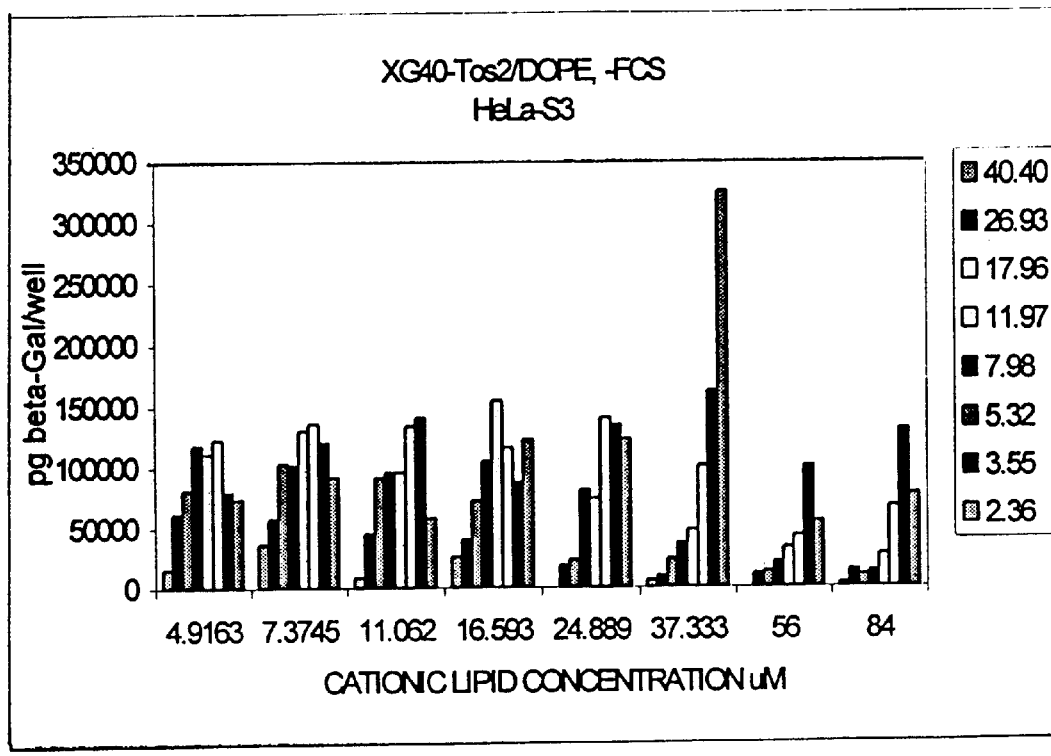
FIG. 14B

FIG. 14C
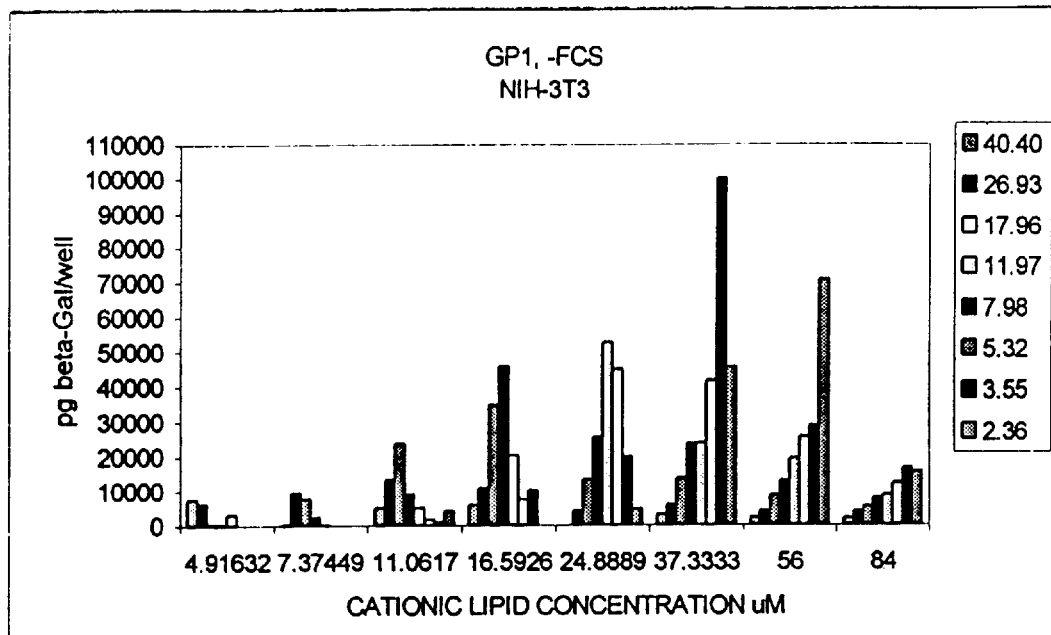
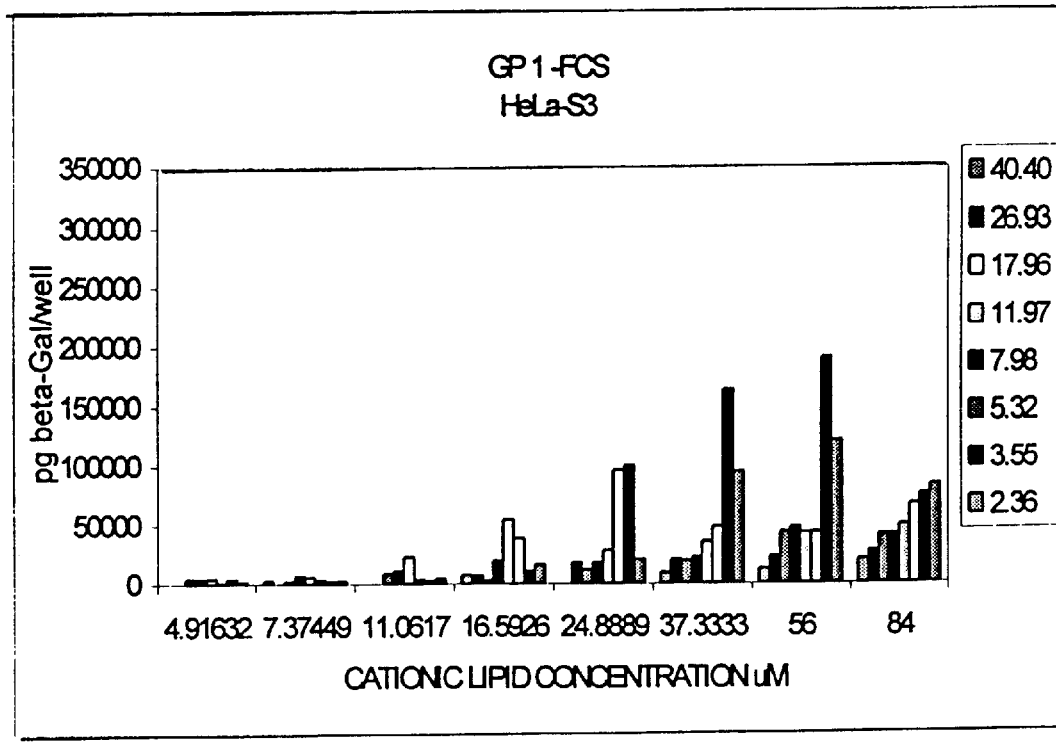
FIG. 14D

AMPHIPHILIC POLYAMINE COMPOUNDS

This application is a divisional of U.S. Ser. No. 09/448,876, filed Nov. 24, 1999, now pending, which claims priority from U.S. Ser. No. 60/111,078, filed Dec. 4, 1998, now abandoned, as well as U.S. Ser. No. 60/110,020, filed Nov. 25, 1998, now abandoned.

FIELD OF THE INVENTION

The invention relates to cationic lipids useful in synthetic gene delivery systems. It relates particularly to amphiphilic cationic lipids having conjugated polyamine groups.

BACKGROUND OF THE INVENTION

Plasmid based, non-viral gene delivery systems represent a promising approach for the treatment of inherited and acquired diseases, and for the development of a new approach to vaccination.[1-8] However, their efficiencies and clinical potencies are limited today due to low level in vitro and in vivo gene product expression.[6,9] The commonly used approaches for increasing expression of synthetic gene delivery systems involve either improving the DNA delivery system,[3,4,9] or optimizing the DNA sequence at the level of either the promoter, enhancer, intron, or terminator.[10-13]

DNA delivery systems include cationic lipids capable of facilitating the transport of biologically active agents, including plasmids, into the cell both in vitro and in vivo, for example, as disclosed in U.S. Pat. No. 4,897,355 to Eppstein et al. and U.S. Pat. No. 5,264,618 to Felgner et al. Synthetic gene delivery systems also comprise the use of cholesterol-based cationic lipids. Lipids such as DC-cholesterol are shown to have both in vivo and in vitro transfection activity[4,14-18] and were the first cationic lipid molecules to be used in human gene therapy clinical trials. It is medically and commercially important to develop improved species of cationic lipids having enhanced transport or transfective potency.

The several panels of FIG. 3 compare the in vitro transfection activity of the "Old XG40 Batch" (FIGS. 3A, 3B and 3C) with that of the "New XG40 Batch" (FIGS. 3D, 3E and 3F) in cell types B16-F0, COS-7 and BJK-21.

Figure 4A:
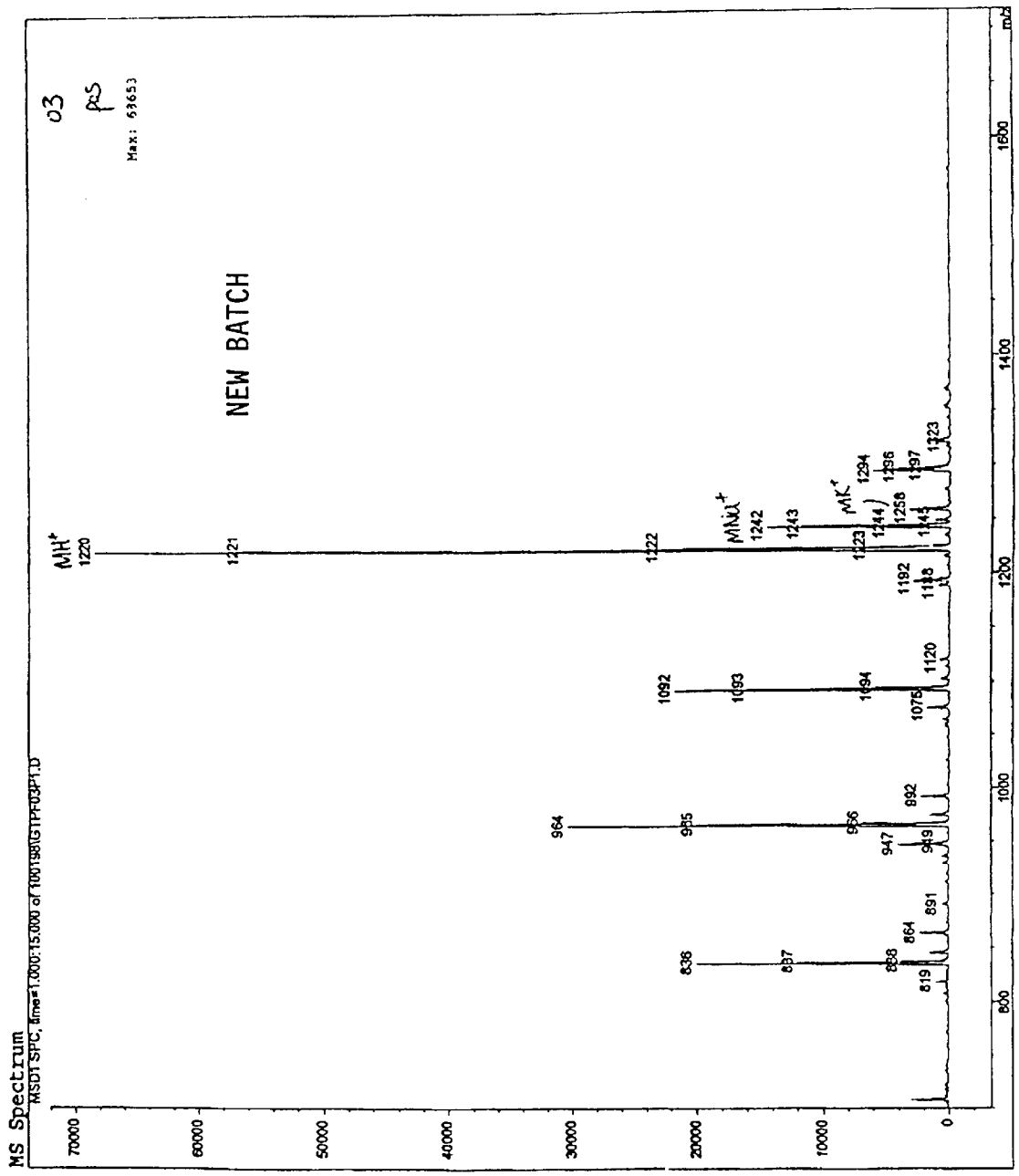
Figure 4B:
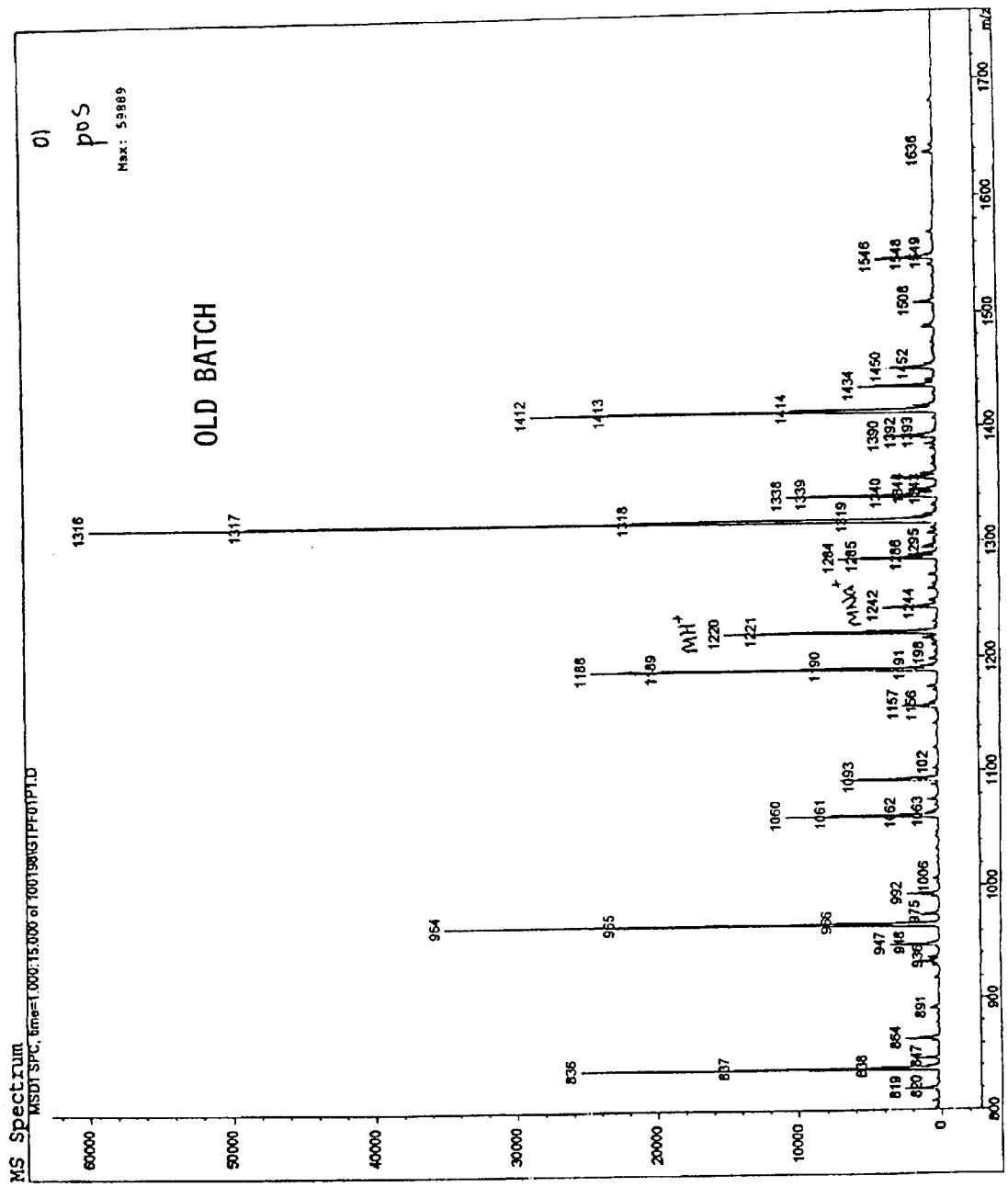

FIGS. 4A and 4B compare the mass spectral analysis of the "New Batch" (FIG. 4A) compounds to those of the "Old Batch" (FIG. 4B) compounds referred to in FIG. 3.

Figure 5A:
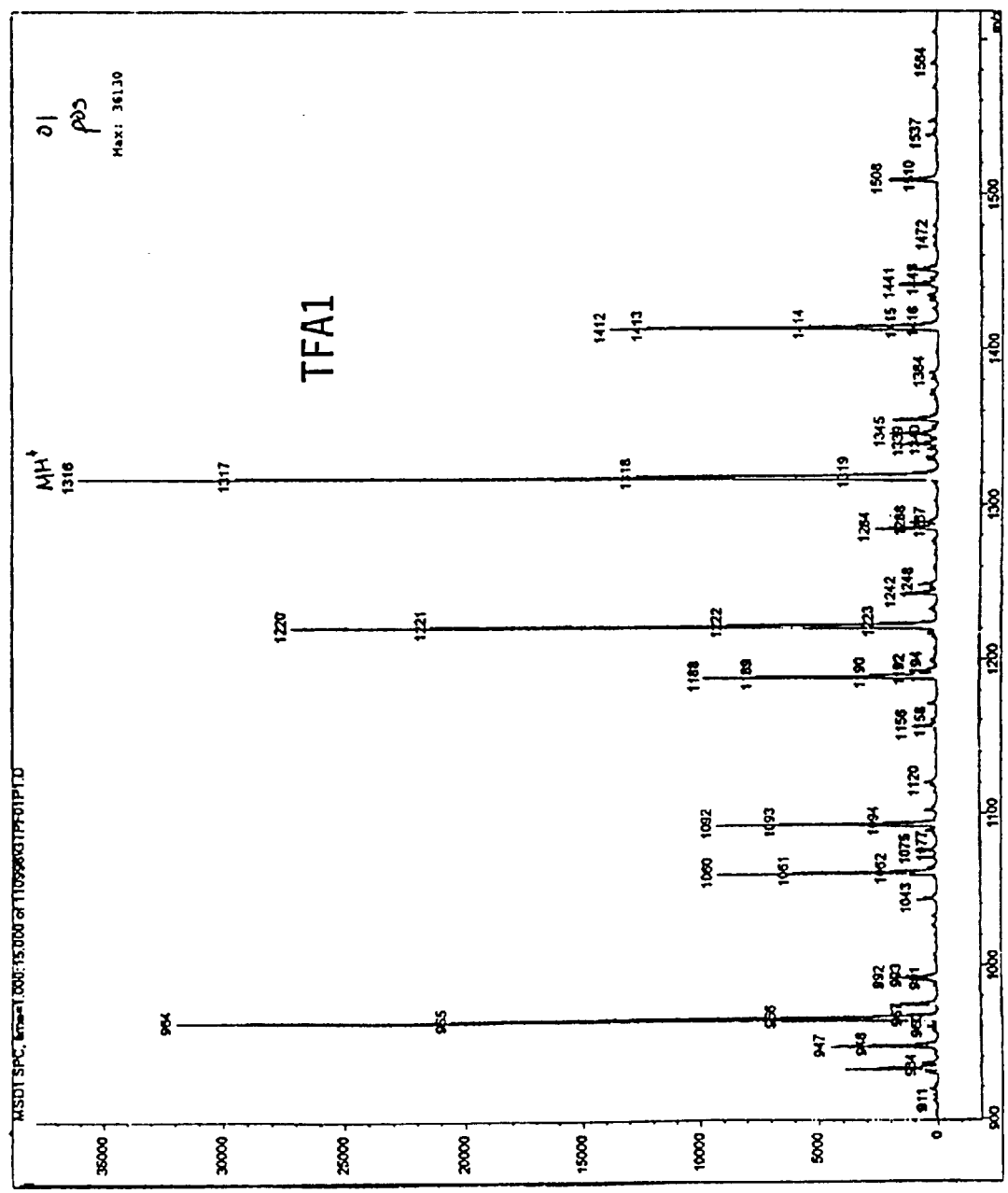
Figure 5B:
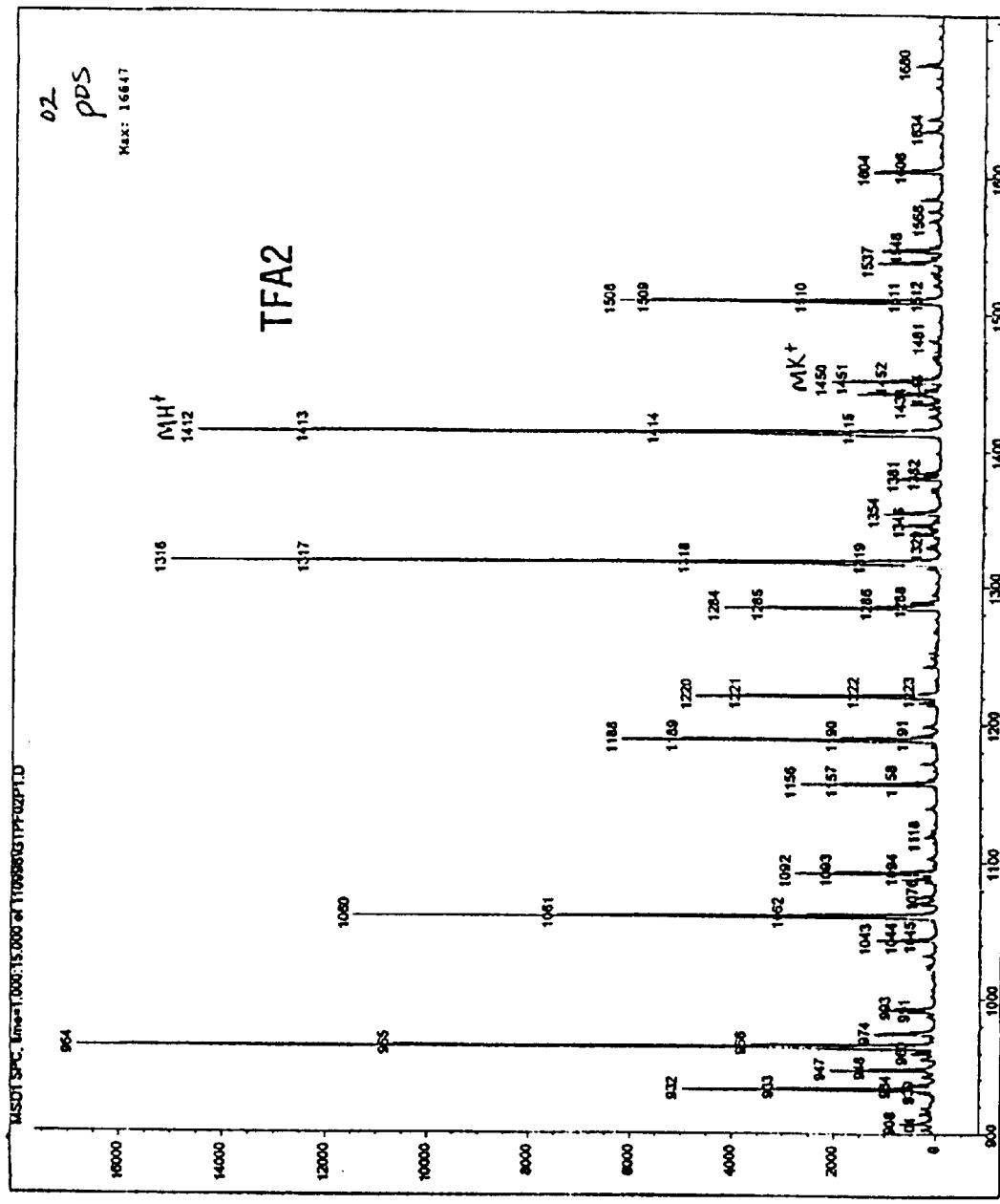
Figure 5C:
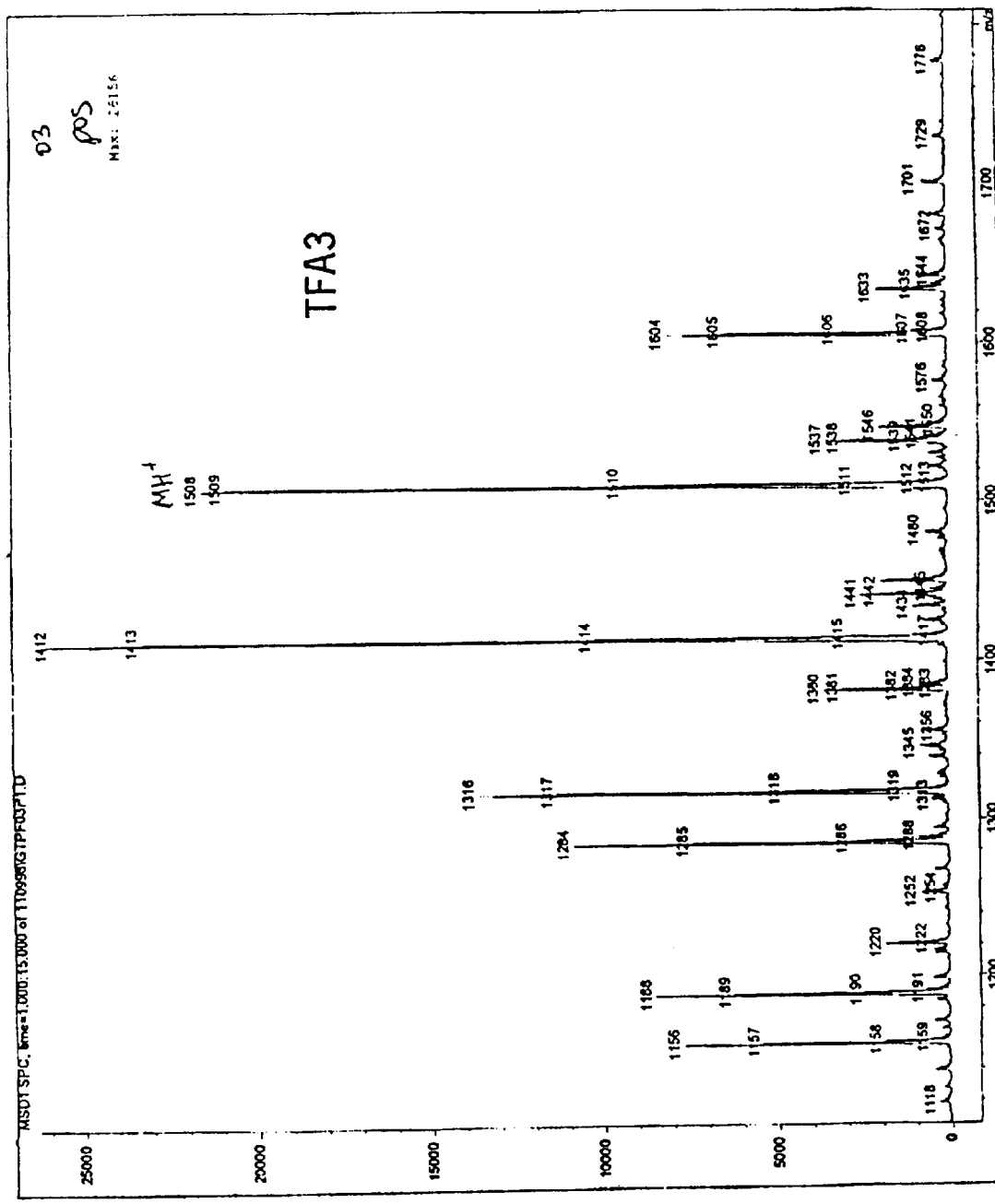
Figure 6A:
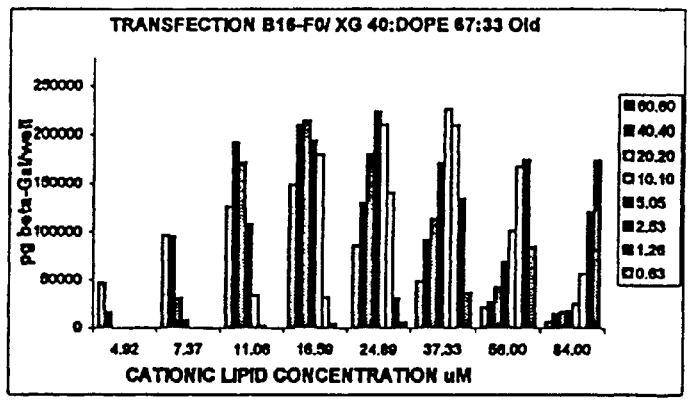
Figure 6B:
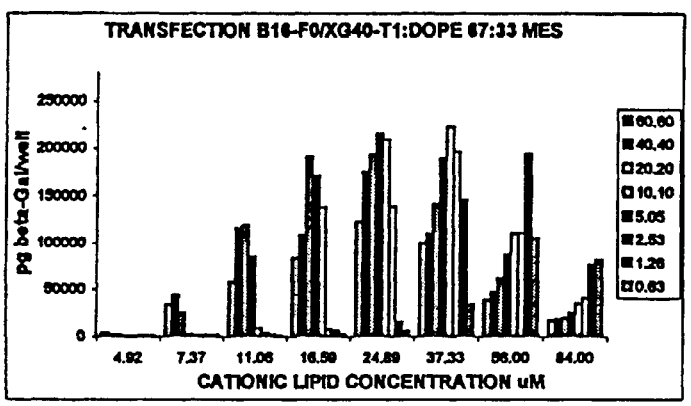
Figure 6C:
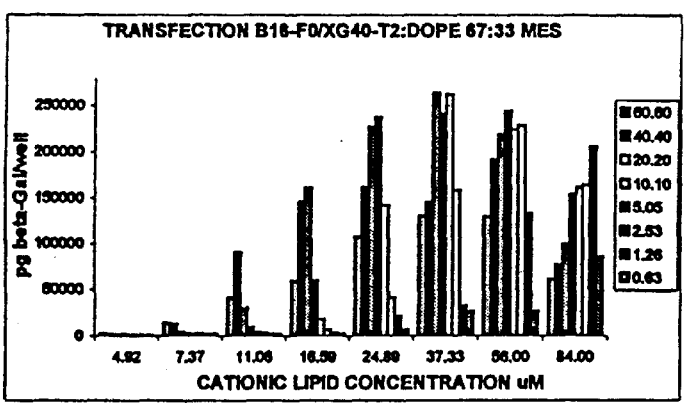
Figure 6D:
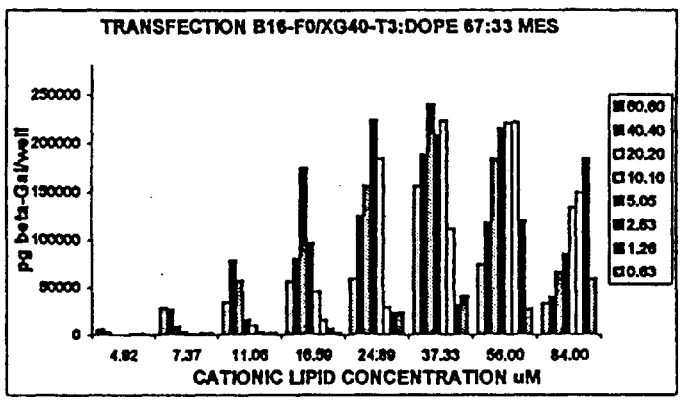
Figure 6E:
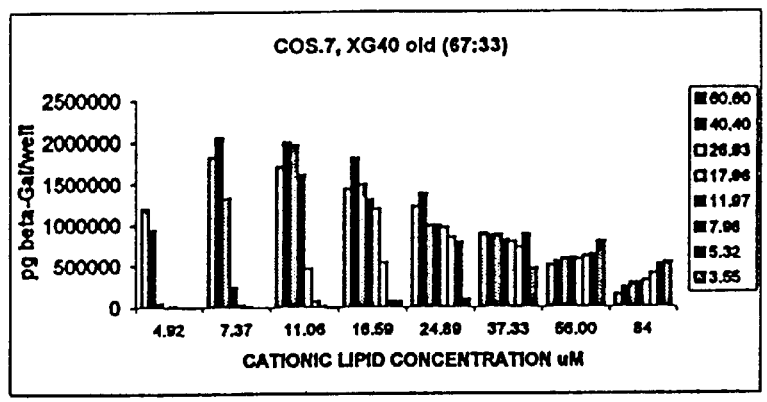
Figure 6F:
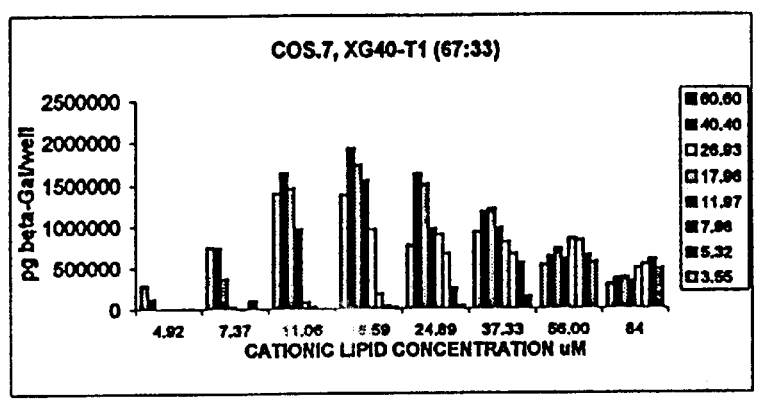
Figure 6G:
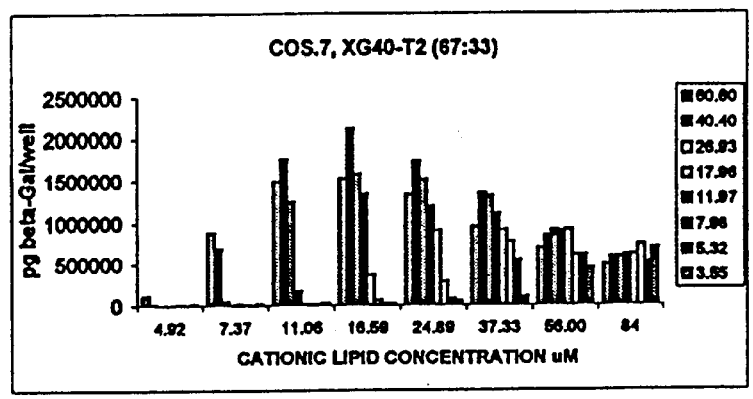
Figure 6H:
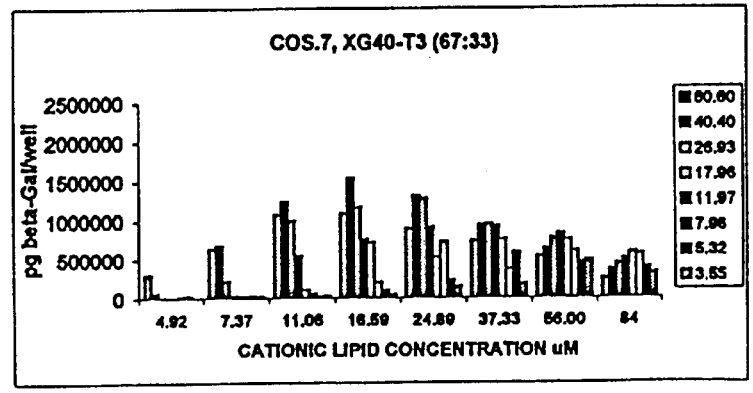
Figure 6I:
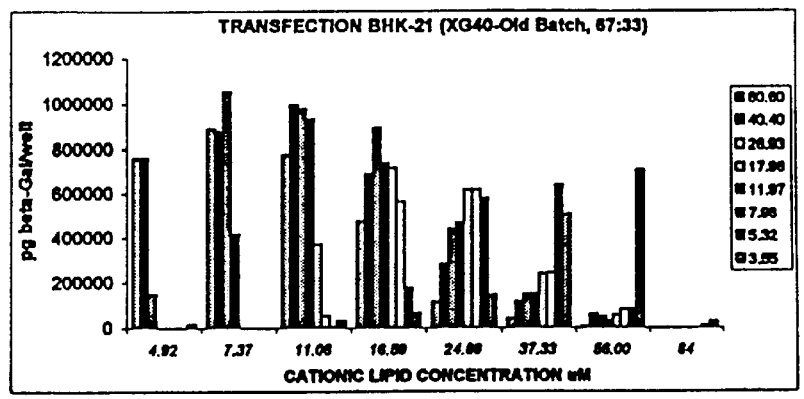
Figure 6J:
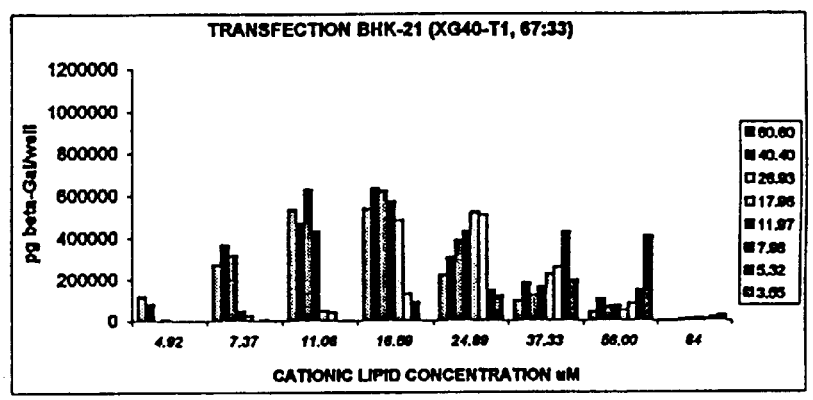
Figure 6K:
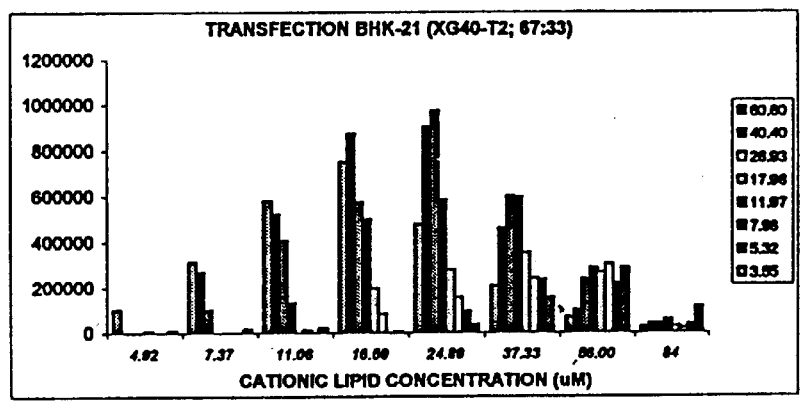
Figure 6L:
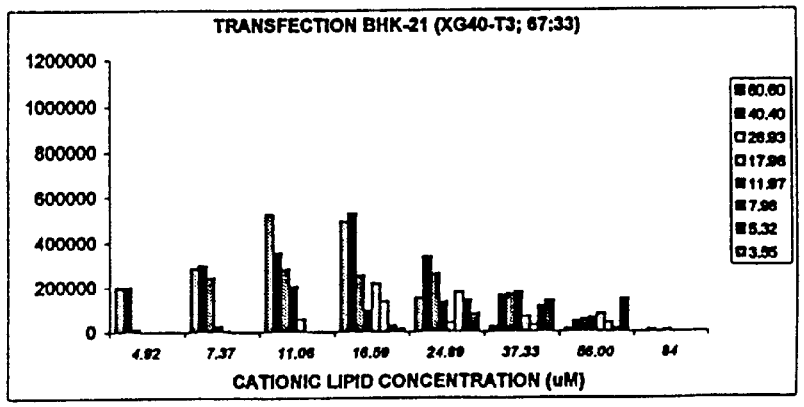
Figure 7A:
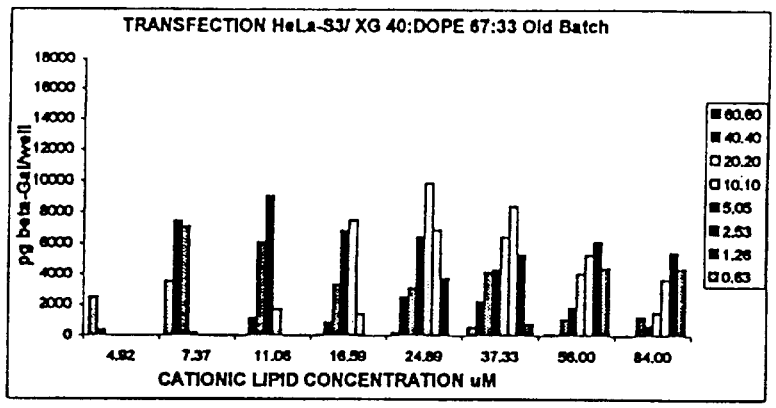
Figure 7B:
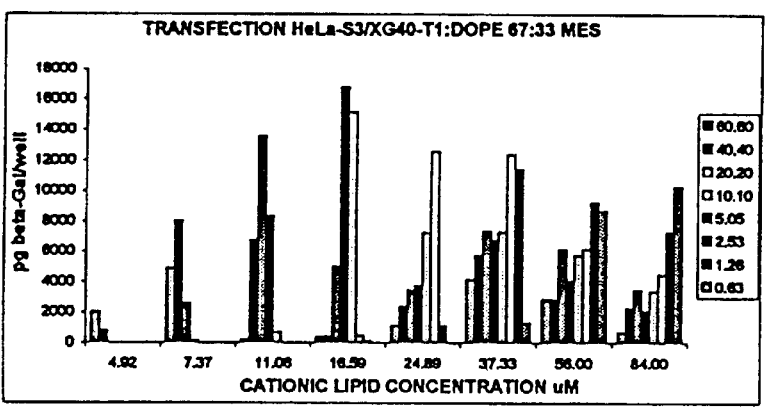
Figure 7C:
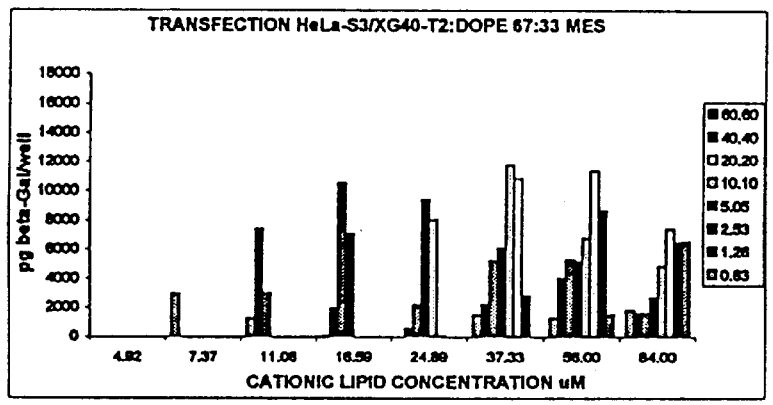
Figure 7D:
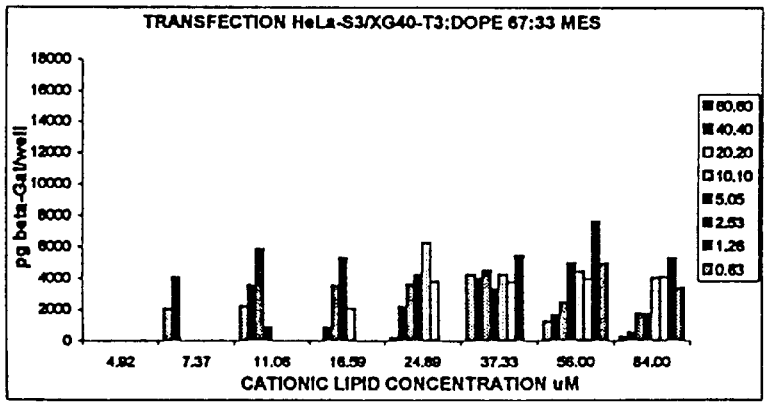
Figure 7E:
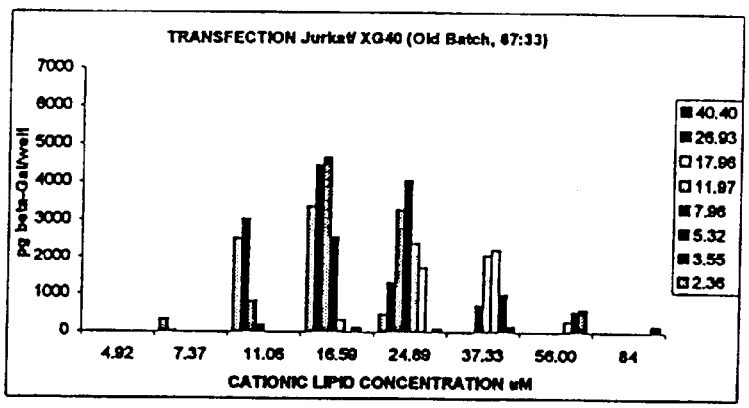
Figure 7F:
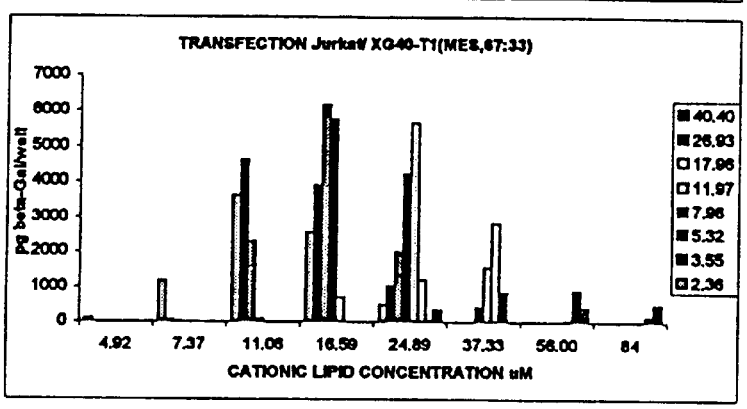
Figure 7G:
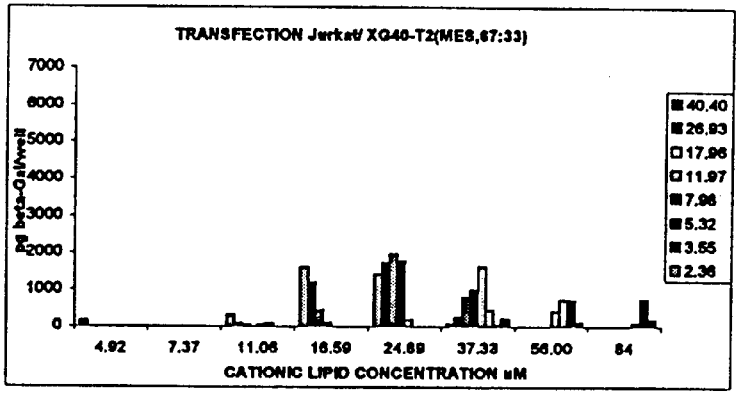
Figure 7H:
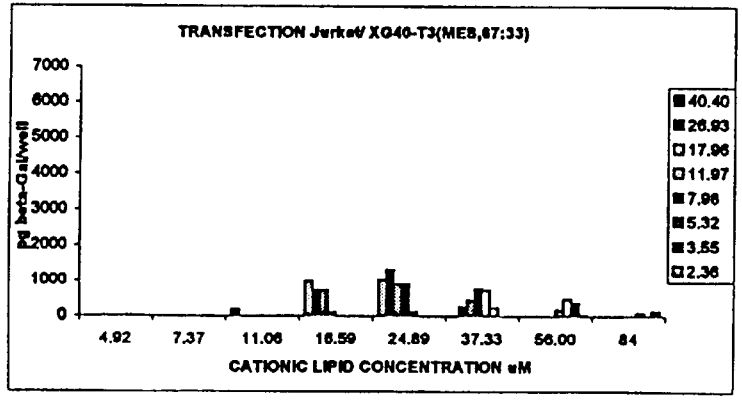
Figure 7I:
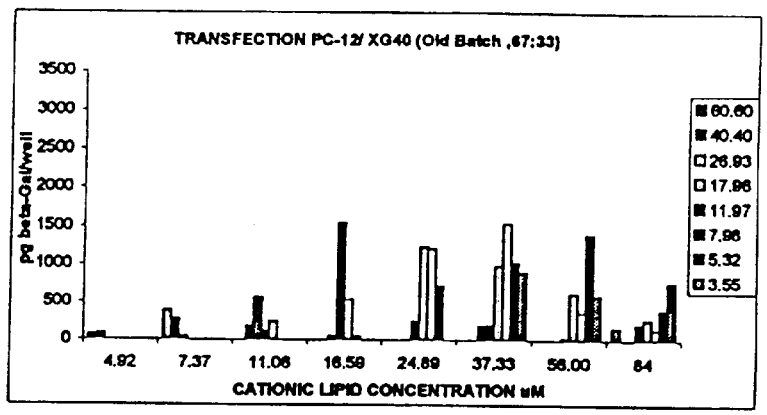
Figure 7J:
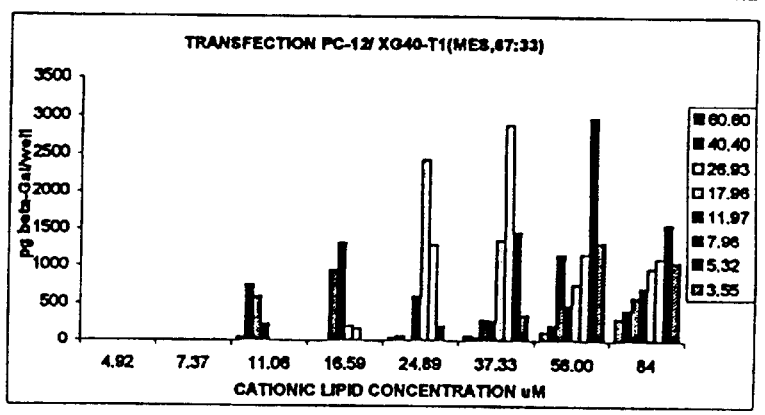
Figure 7K:
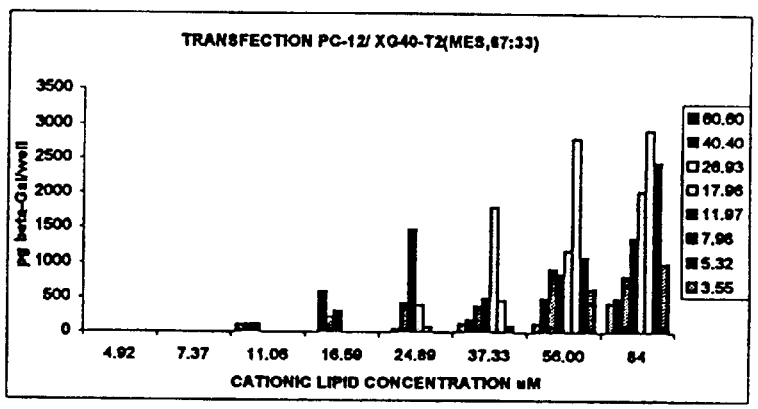
Figure 7L:
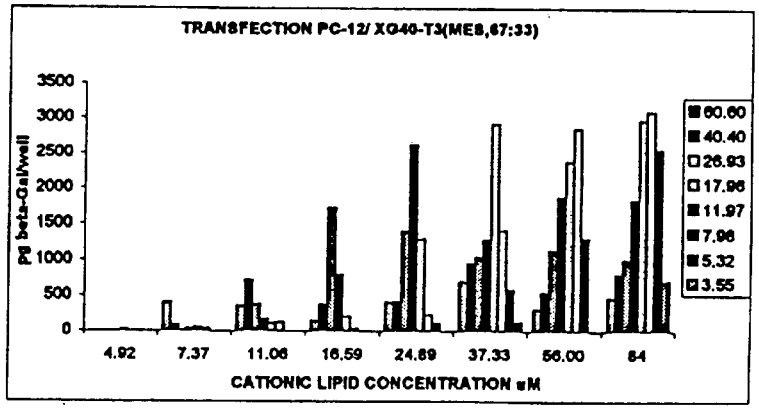
Figure 7M:
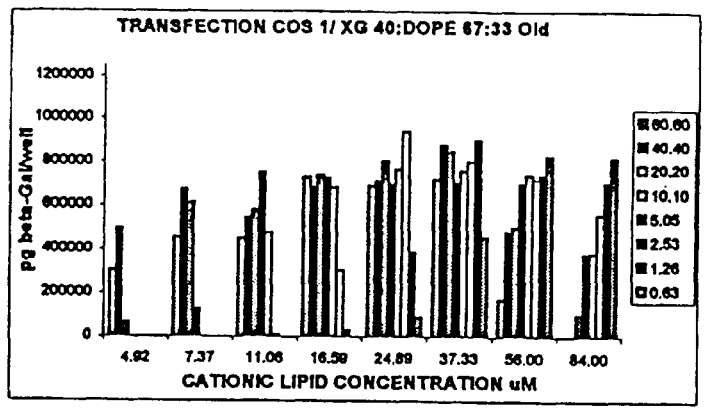
Figure 7N:
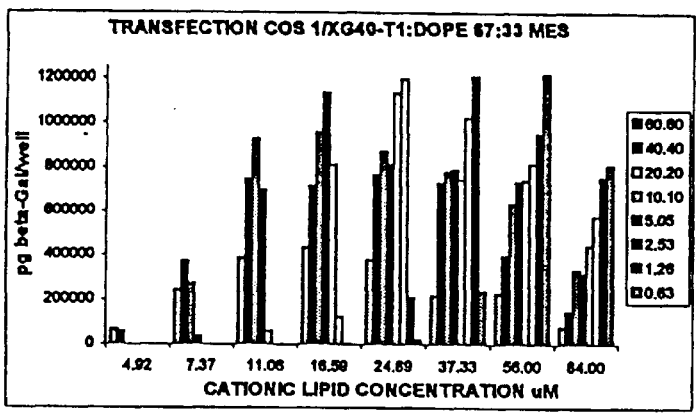
Figure 7O:
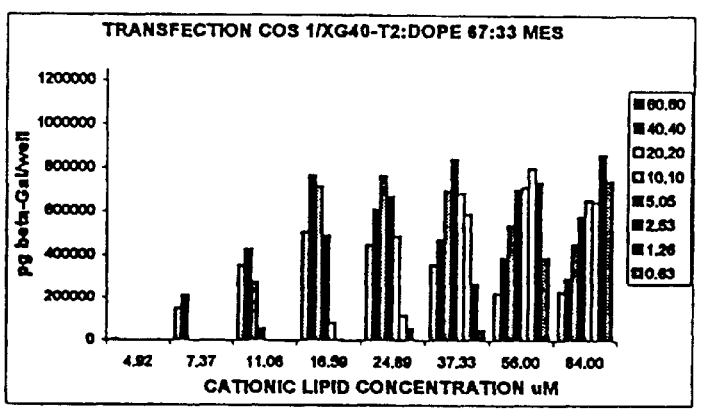
Figure 7P:
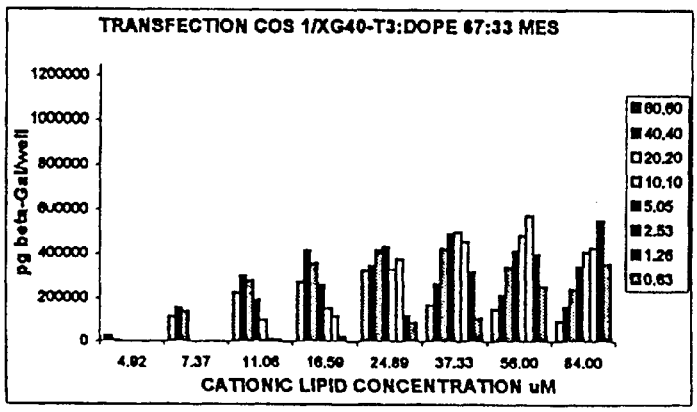
Figure 7Q:
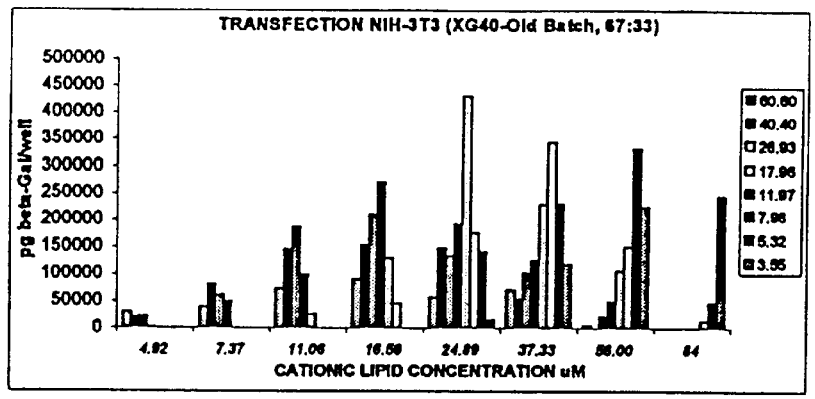
Figure 7R:
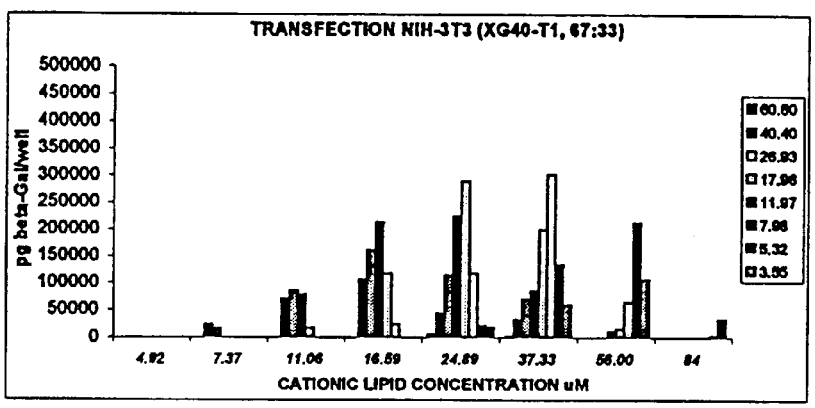
Figure 7S:
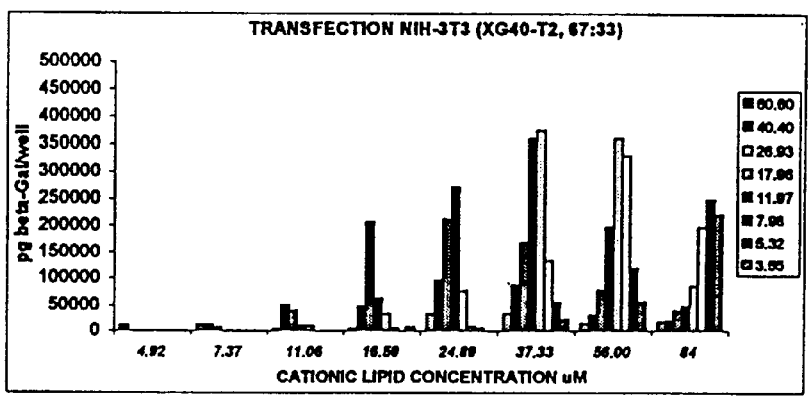
Figure 7T:
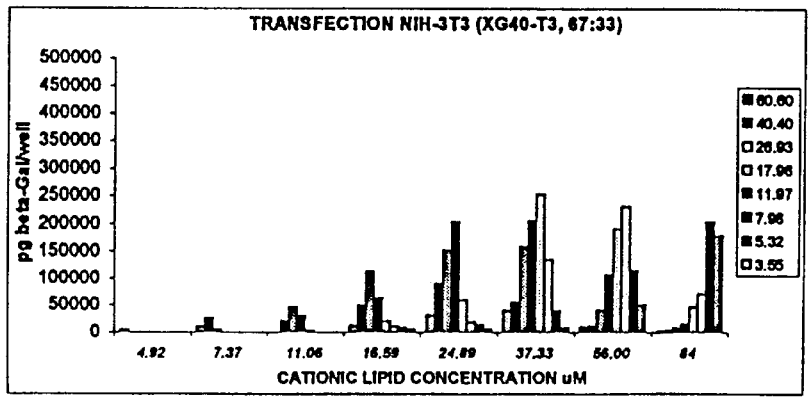
Figure 7U:
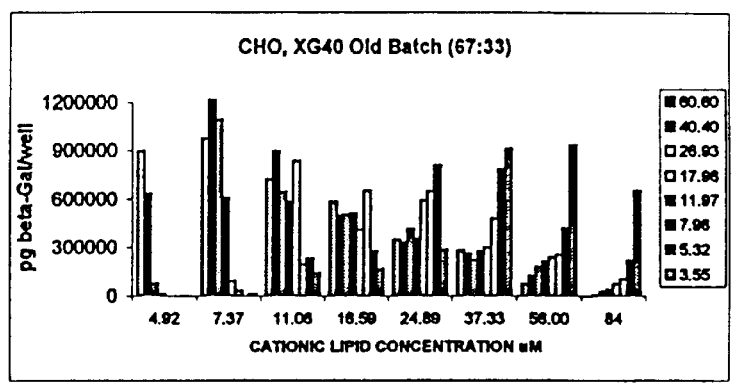
Figure 7V:
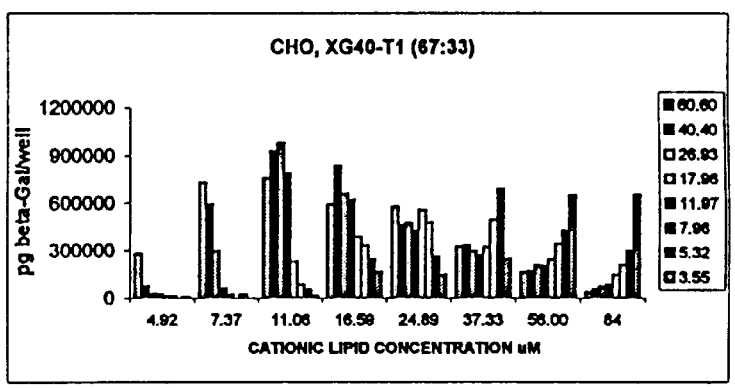
Figure 7W:
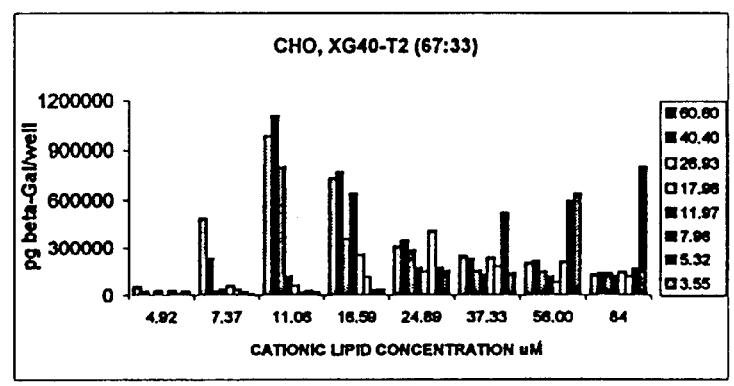
Figure 7X:
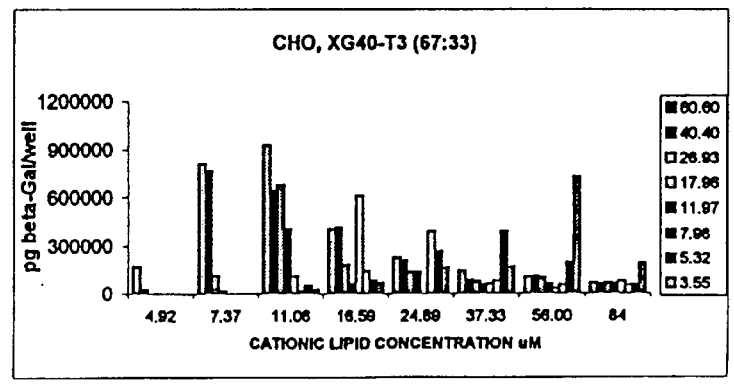
Figure 7Y:
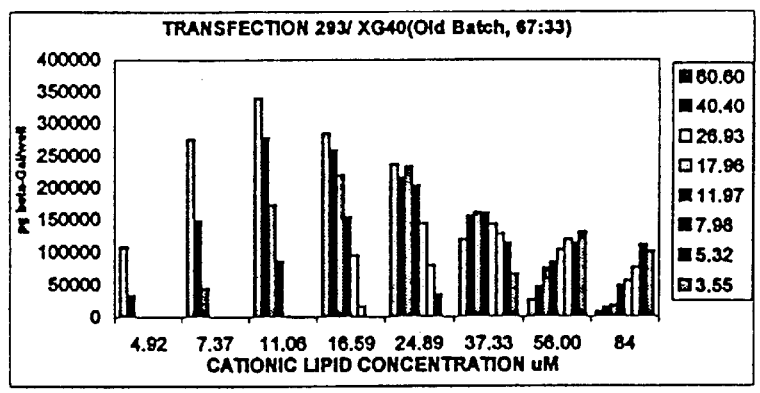
Figure 7Z:
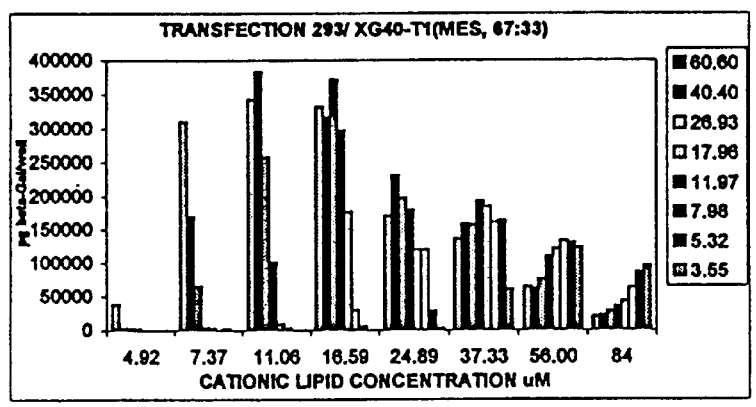
Figure 7A:
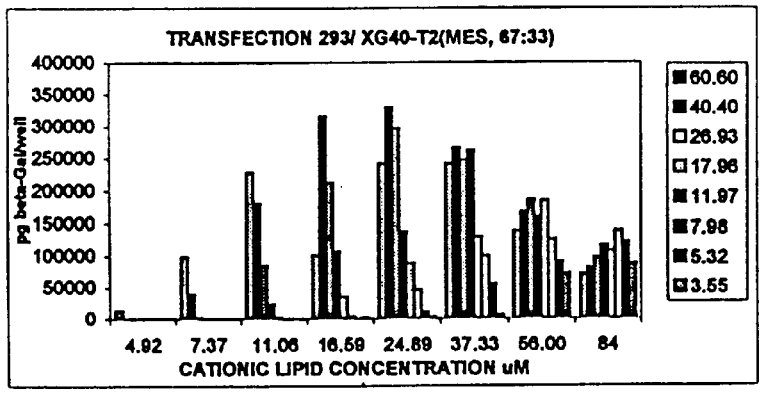
Figure 7B:
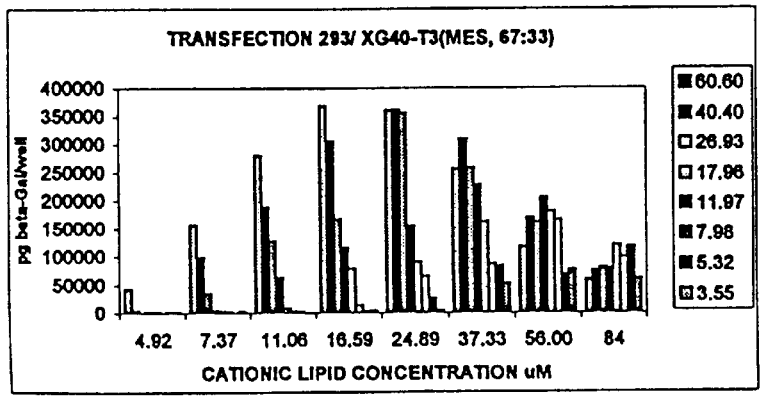
Figure 7C:
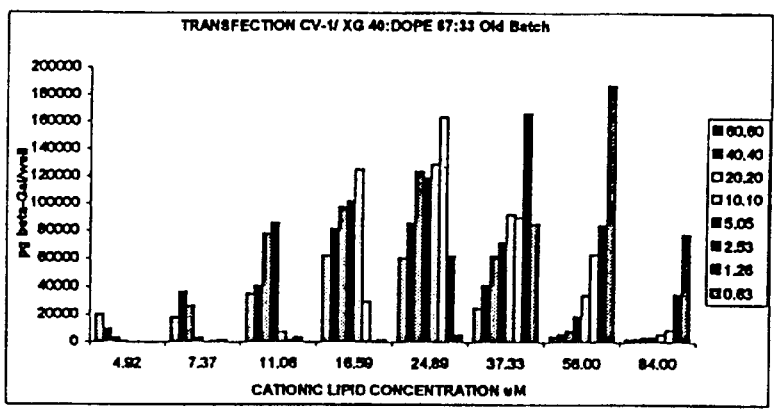
Figure 7D:
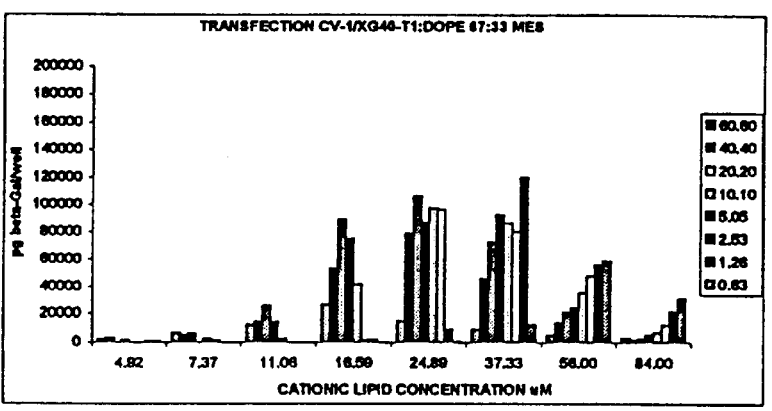
Figure 7E:
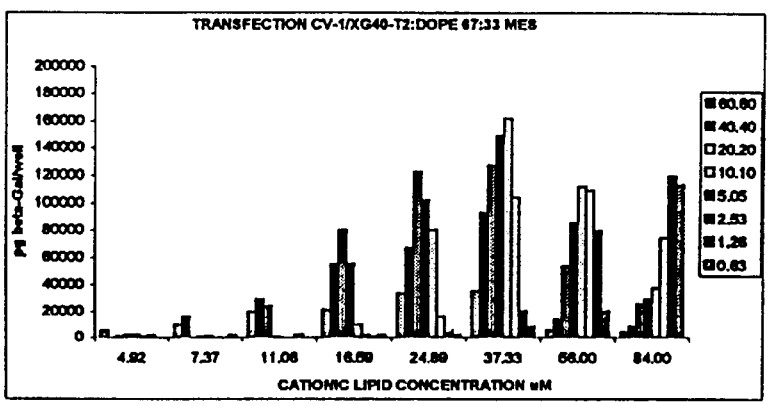
Figure 7F:
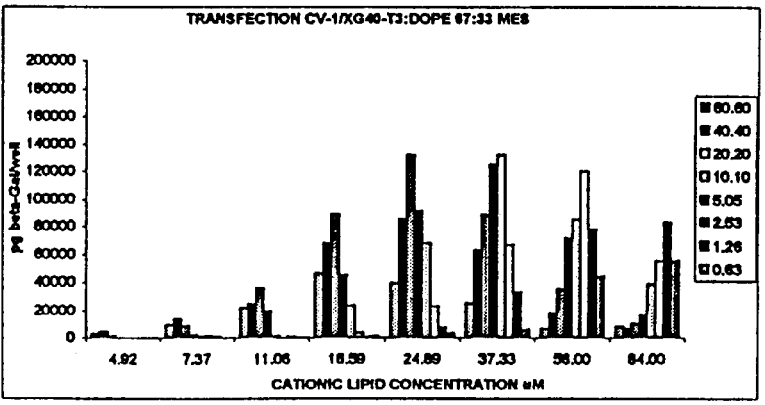

FIGS. 5A, 5B and 5C show the mass spectral analysis of compounds of the invention when conjugated with increasing numbers of trifluoroacetic acid molecules: FIG. 5A=TFA1, FIG. 5B=TFA2, FIG. 5C=TFA3.

The panels of FIG. 6 show that TFA conjugation of the new XG40 batch restores the transfection potency when tested in cell types B 16-F0, Cos-7 and BHK-21. Thus, FIGS. 6A, 6B, 6C and 6D relate to studies employing B16-F0 cell type, FIGS. 6E, 6F, 6G and 6H relate to studies employing COS.7 cell type and FIGS. 6I, 6J, 6K and 6L relate to studies employing BHK-21 cell type.

The panels of FIG. 7 compare the transfection effectiveness of a series of trifluoroacetylated XG40 derivatives having increasing amounts of trifluoroacetate conjugated to the primary amine groups with the "Old Batch" in 8 additional cell types. Thus, FIGS. 7A, 7B, 7C and 7D relate to studies employing HeLa-S3 cells, FIGS. 7E, 7F, 7G and 7H relate to studies employing Jurkat cell;, FIGS. 7I, 7J, 7K and 7L relate to studies employing PC12 cells, FIGS. 7M, 7N, 7O and 7P relate to studies employing COS.1 cells, FIGS. 7Q, 7R, 7S and 7T relate to studies employing NIH-3T3 cells, FIGS. 7U, 7V, 7W and 7X relate to studies employing CHO cells, FIGS. 7Y, 7Z, 7AA and 7BB relate to studies employing 293 cells and FIGS. 7CC, 7DD, 7EE and 7FF relate to studies employing CV-1 cells.

Figure 8B:
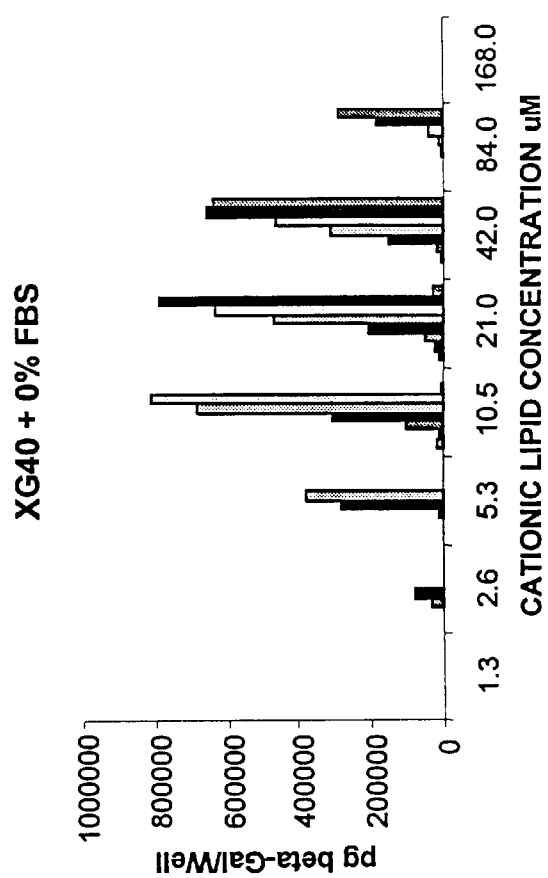
Figure 8A:
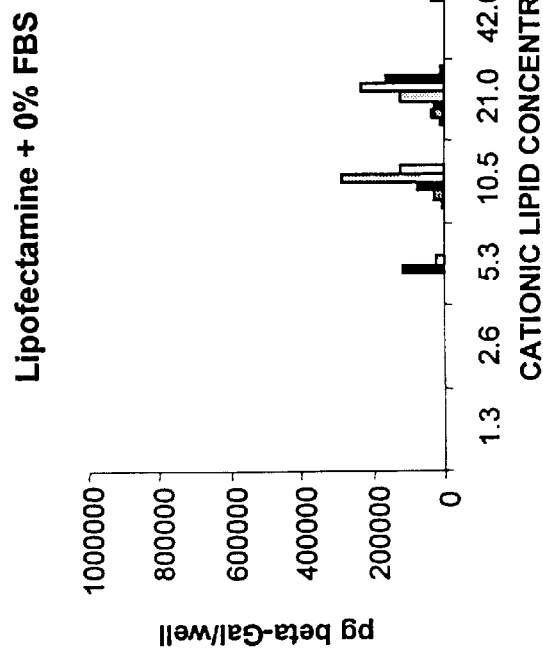

FIGS. 8A and 8B compare the activity of the trifluoroacetylated XG40 product (8B) with LipofectAMINE® (Life Technologies, Inc.) (8A).

Figure 9B:
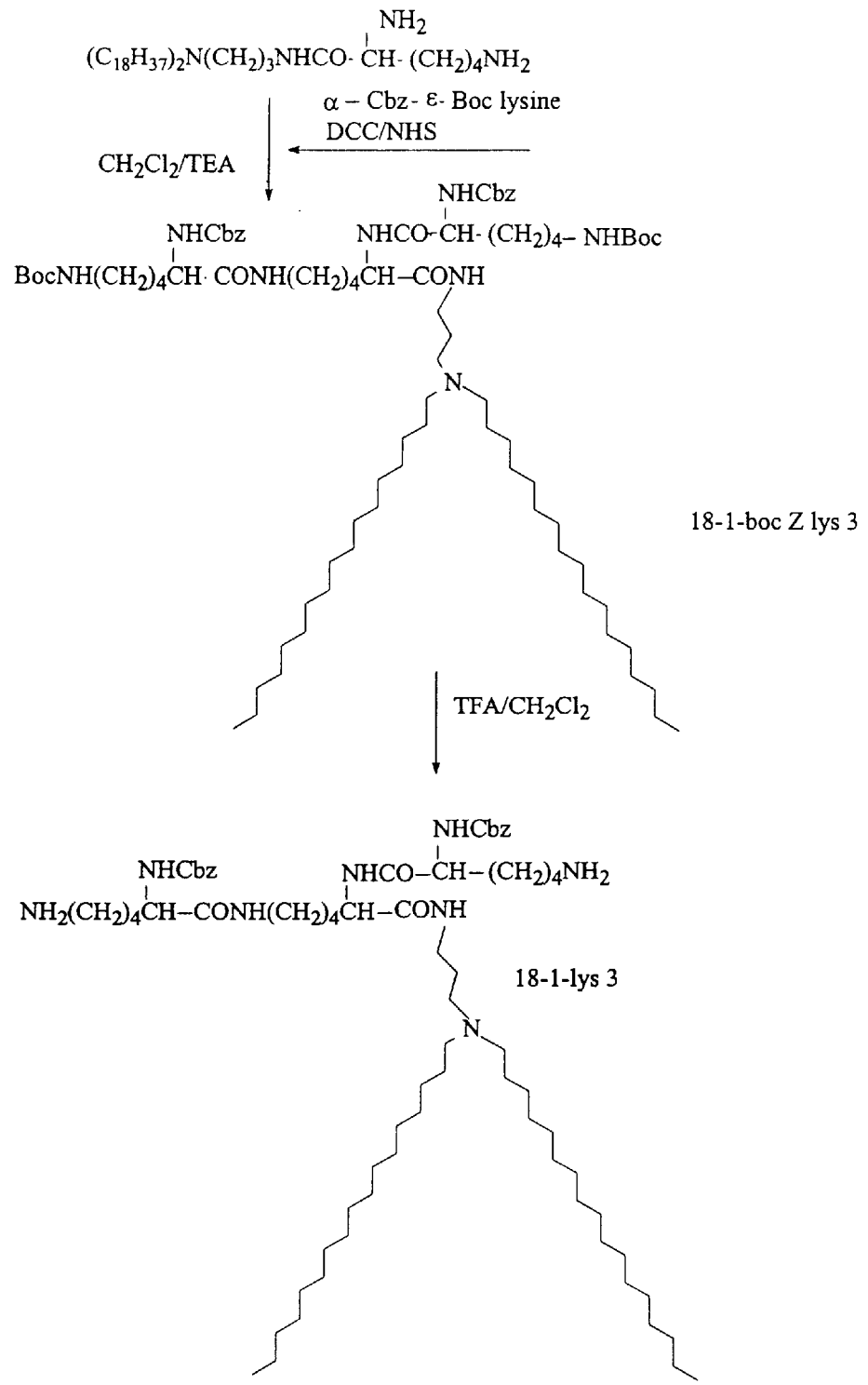
Figure 12A:
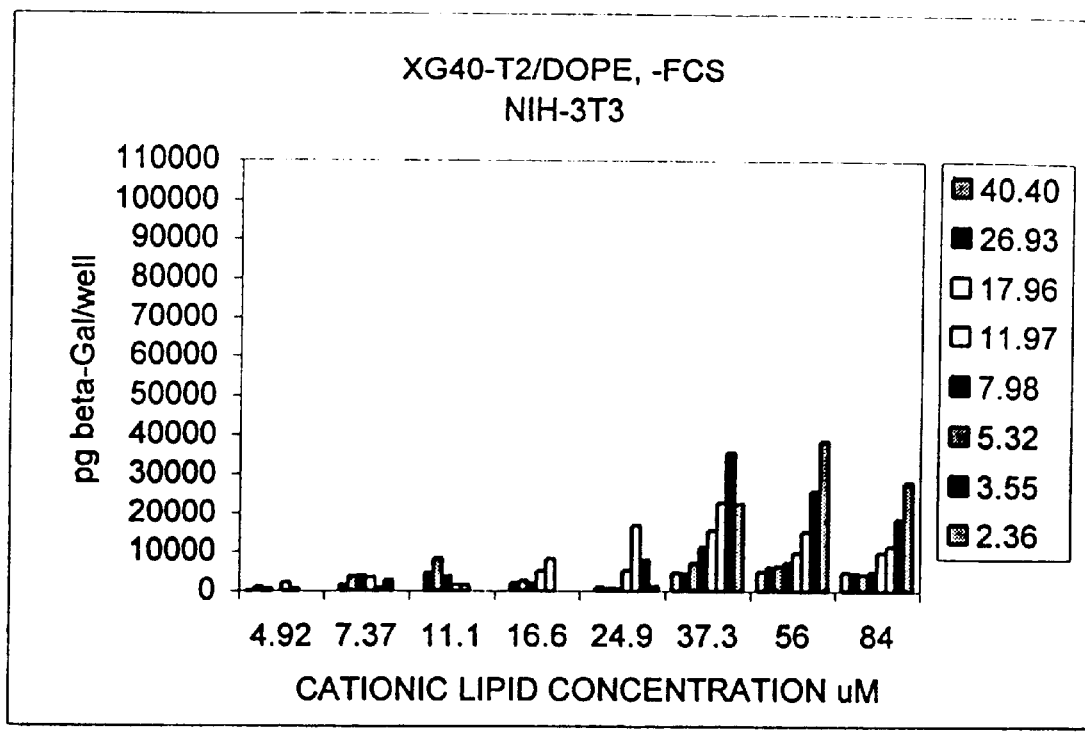
Figure 12B:
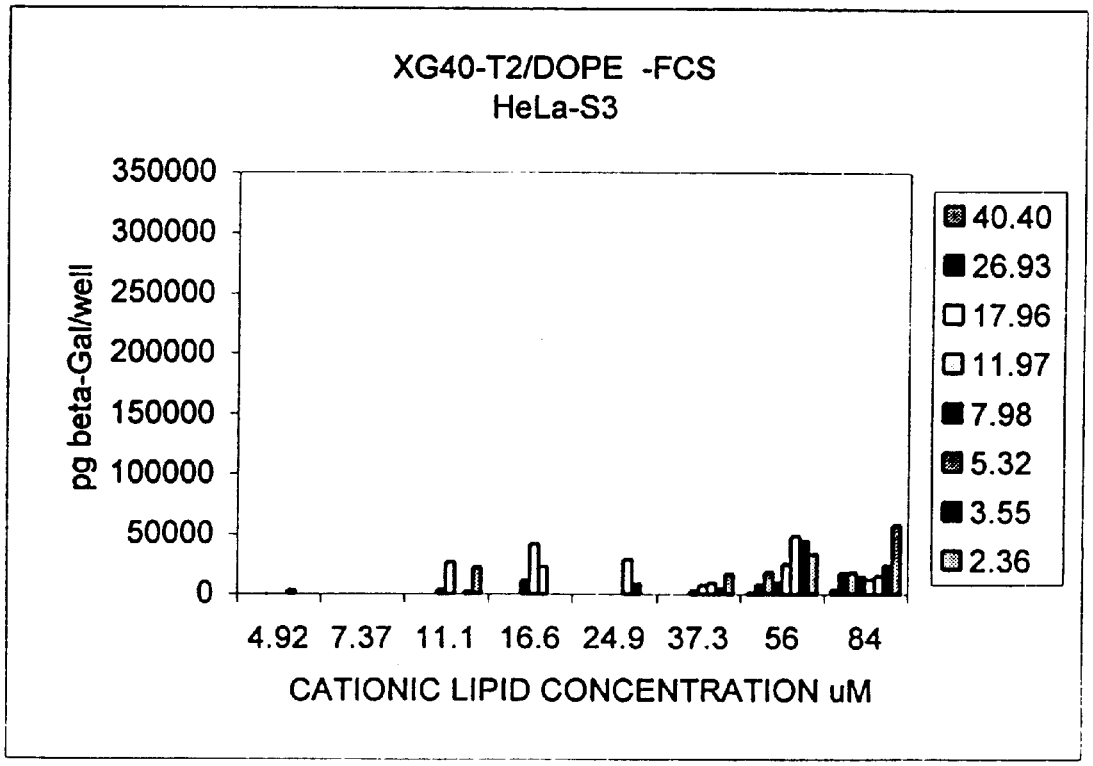
Figure 13A:
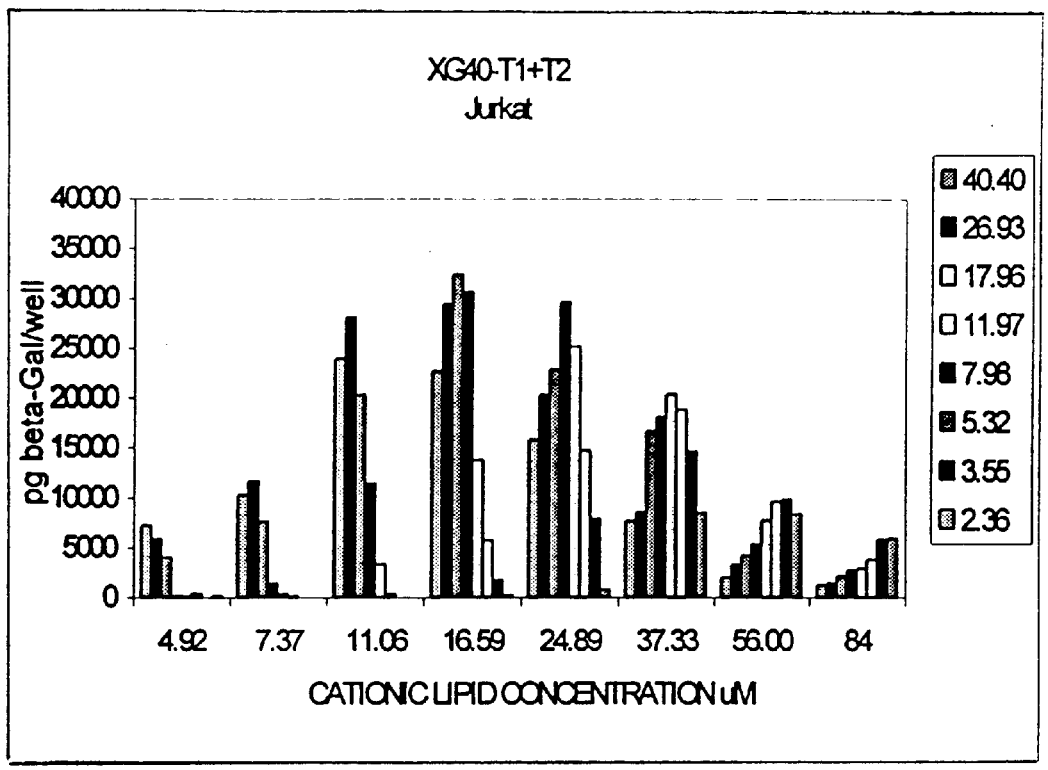
Figure 13B:
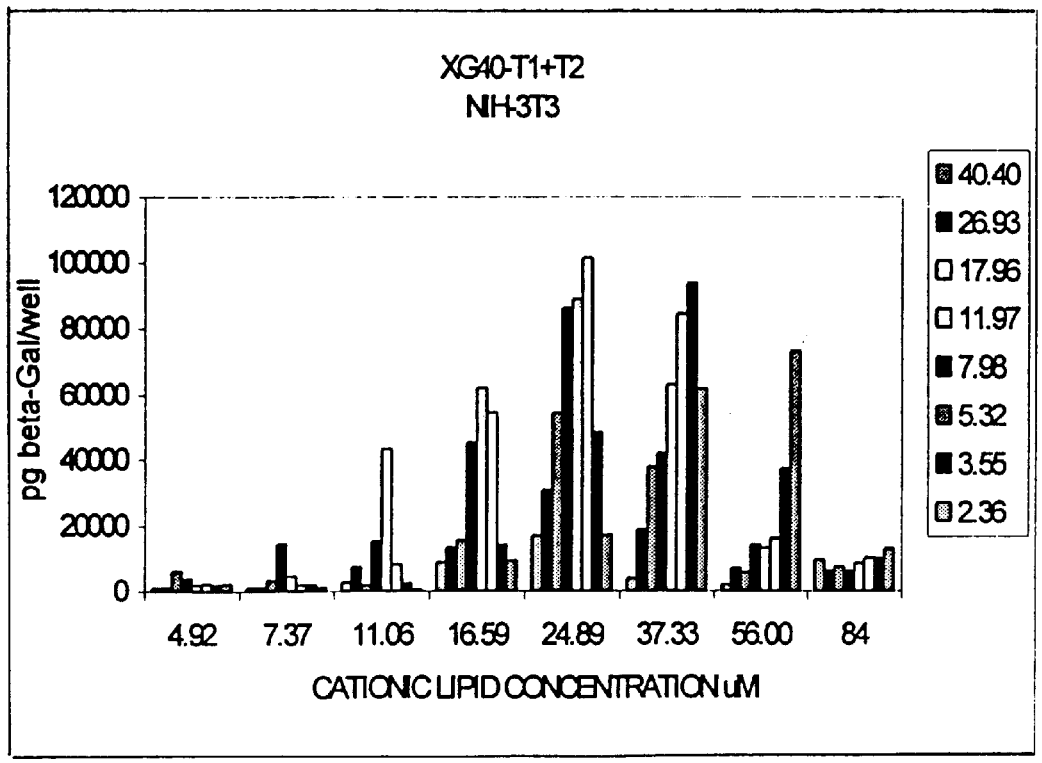
Figures 15A, 15B:
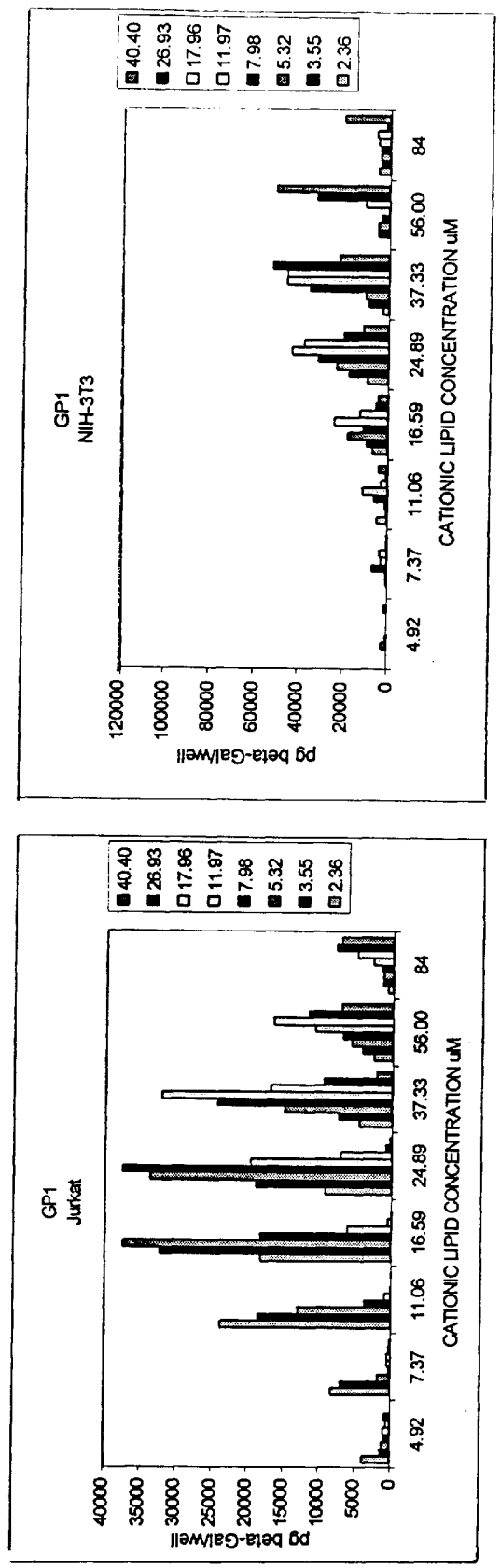
Figure 15D:
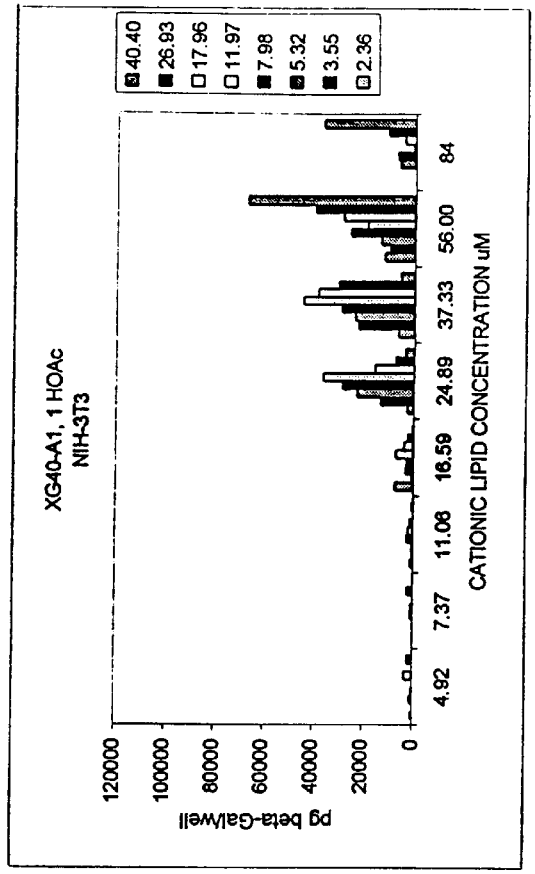
Figure 15C:
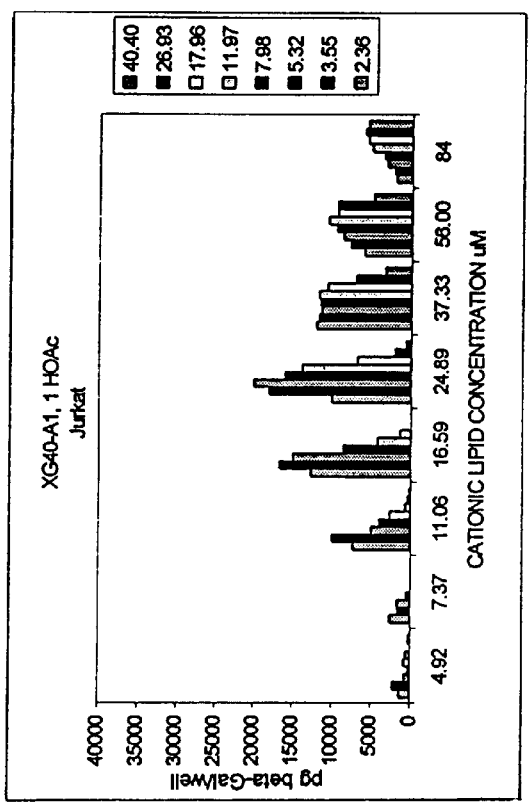
Figure 15F:
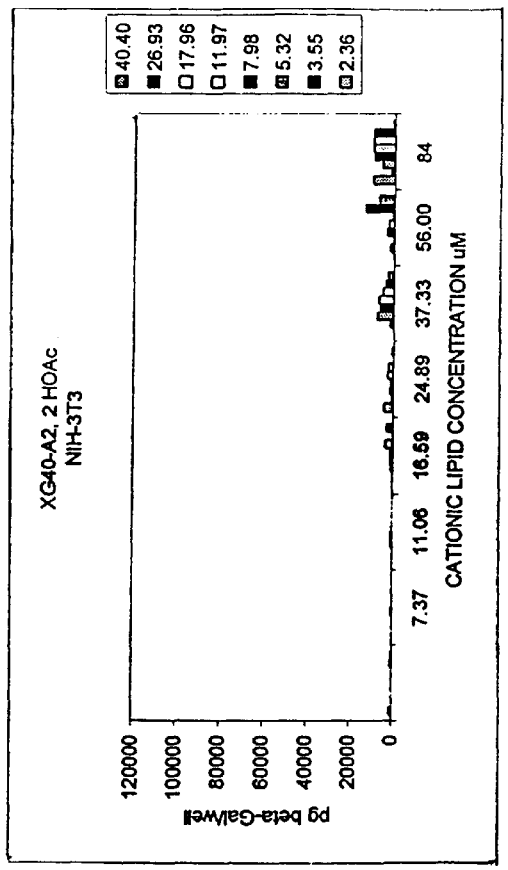
Figure 15E:
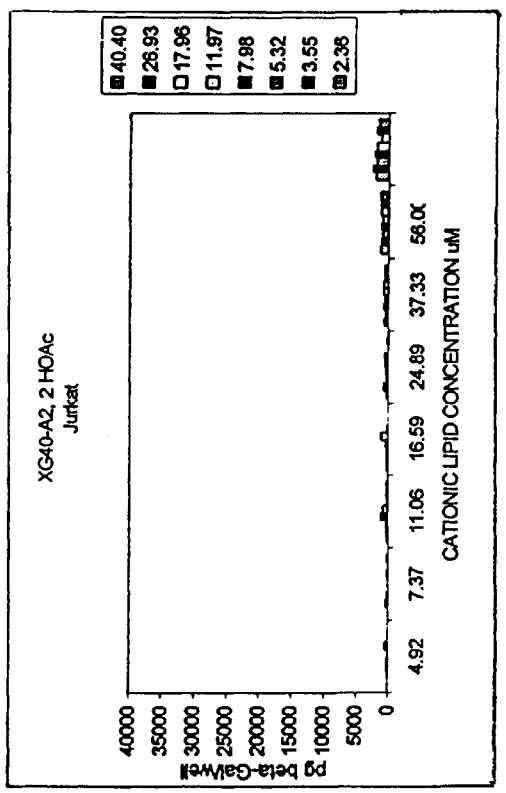

The panels of FIG. 9 present a multistep synthetic scheme for the preparation of 18-1-lys 5Tϵ. Thus, FIG. 9A presents steps 1 and 2 of the Reheme, FIG. 9B presents step 3 of the scheme; and FIG. 9C presents step 4 of the scheme.

FIG. 10 presents synthetic schemes for preparation of 18-1-lys 5Tϵ analogues with different fatty chains (10A) and different lysine groups (10B).

FIGS. 11A–11D present assay results for the activity of H-Arg(Tos)-18-1-HCl on cell types NIH-3T3 and HeLa-S3.

FIGS. 12A–12D present assay results for the activity of [lys-5-18-1-Tfa(2)] on cell types NIH-3T3 and HeLa-S3.

FIGS. 13A–13D present assay results for the activity of [lys-5-18-1-Tfa(1)]+[lys-5-18-1-Tfa(2)] on cell types NIH-3T3 and HeLa-S3.

FIGS. 14A–14D present assay results for the activity of [lys-5-18-1-Tos(2)] on cell types NIH-3T3 and HeLa-S3.

FIGS. 15A–15F present assay results for the activity of [XG40-A1]+[XG40-A2] on cell types Jurkat and NIH-3T3.

DETAILED DESCRIPTION OF THE INVENTION

Certain amphipathic polyamine compounds have been found to be superior to known cationic amphiphiles in their ability to transfect cells and to deliver genes intracellularly. The compounds are characterized by a dialkylamine joined through an amide linker to a derivatized polyamidino chain. These compounds have the general structure (I):

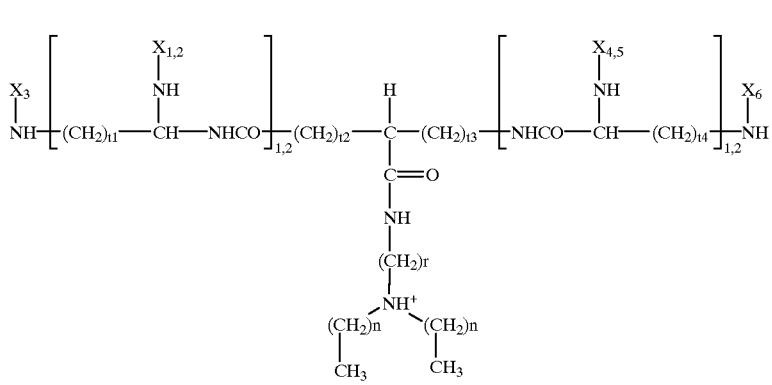

wherein $X_1$, $X_2$, $X_3$, $X_4$, $X_5$ and $X_6$ are independently selected from the group consisting of amine-protecting or amine-blocking groups, which may comprise any molecule containing a carboxyl or sulfonyl group that is capable of forming an amide bond with the available amine groups of the compound. Such X groups can be, but are not limited to, for example, amino acids, tosylate (Tos), benzyloxycarbonyl (Cbz), t-butyloxy-carbonyl (Boc), acetate, and trifluoroacetate groups.

In a preferred embodiment of the invention, $X_1$, $X_2$, $X_3$, $X_4$, $X_5$ and $X_6$ are independently selected from the group consisting of:

H;

tosylate (Tos);

benzyloxycarbonyl (Cbz);

t-butyloxycarbonyl (Boc);

$H_3C-C(=O)$; and $F_3C-C(=O)$;

r is an integer from 1 to 4;

n is an integer from 7 to 21; and each t is independently an integer from 0 to 5.

In another preferred embodiment, the amphipathic polyamines of the invention have the structure (II):

$H_3C-C(=O)$; and $F_3C-C(=O)$;

each t is independently an integer from 0 to 5;

r is an integer from 1 to 4; and n is an integer from 7 to 21.

In particularly preferred embodiments, the polyamidine chain comprises lysine residues wherein r is 3; t is 4, and n is 17. In alternate preferred embodiments fatty acids of the dialkyl chain of these compounds having the formula $-N-((CH_2)_n-CH_3)_2$, wherein n is an integer from 7 to 21, can contain from 1 to 6 double bonds. The compounds can comprise X groups in any combination of amine protecting or amine blocking groups. In a most preferred embodiment, the compounds can comprise X groups in any combination of tosylate and trifluoroacetate conjugate species and in any combination of X positions. For example $X_1$, $X_3$ and $X_6$ are fluoroacetate, or $X_1$ is tosylate, $X_2$ is fluoroacetate, $X_5$ is tosylate, and the like, are within the scope of the invention.

Figure 1:
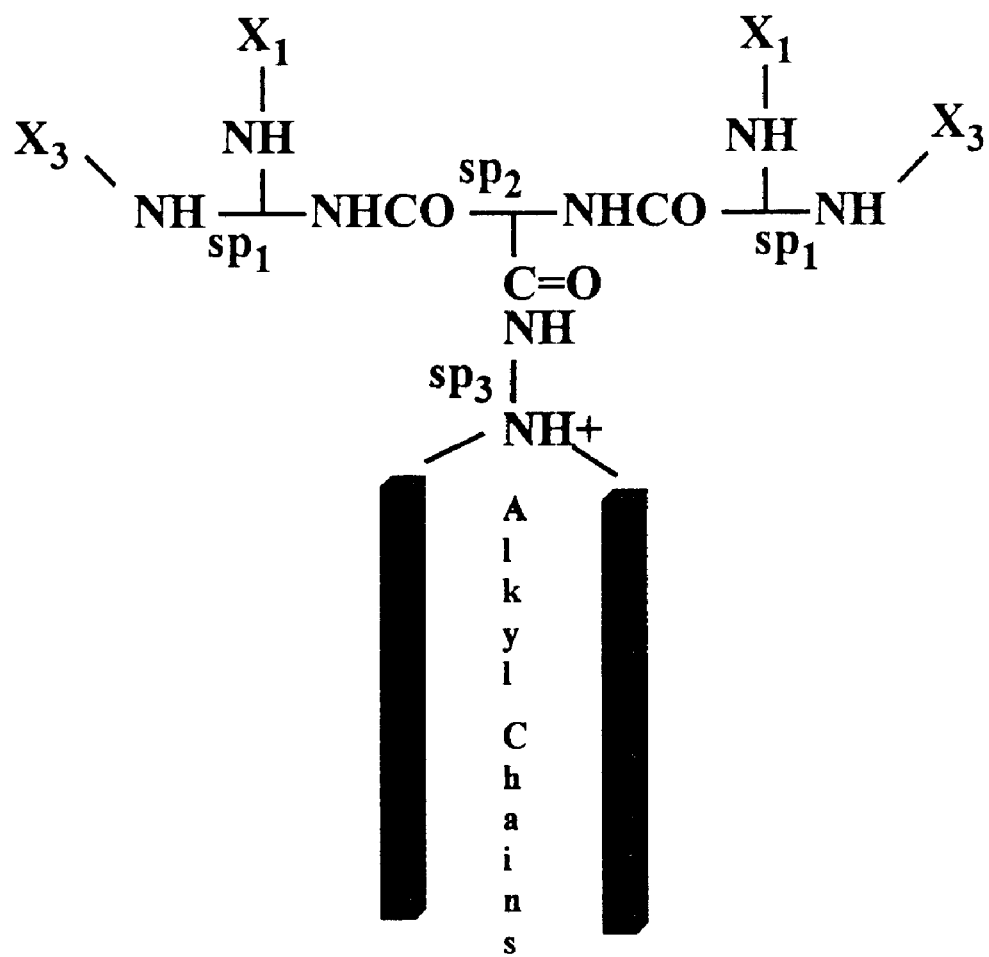
FIG. 1 shows the general structure of compounds of the XG39 species. X is an acetate or trifluoroacetate group and sp is the alkyl spacer between the amidine-containing groups.
Figure 2:
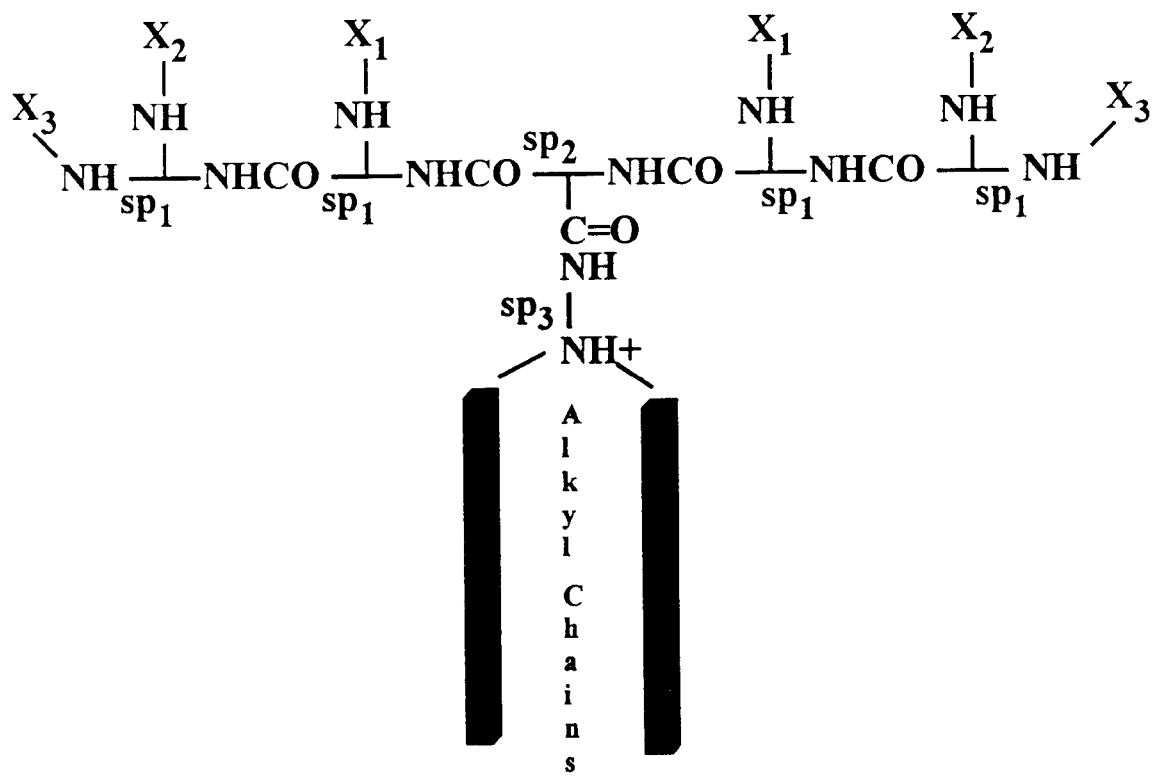
FIG. 2 shows the general structure of compounds of the XG40 group.
Figure 3A:
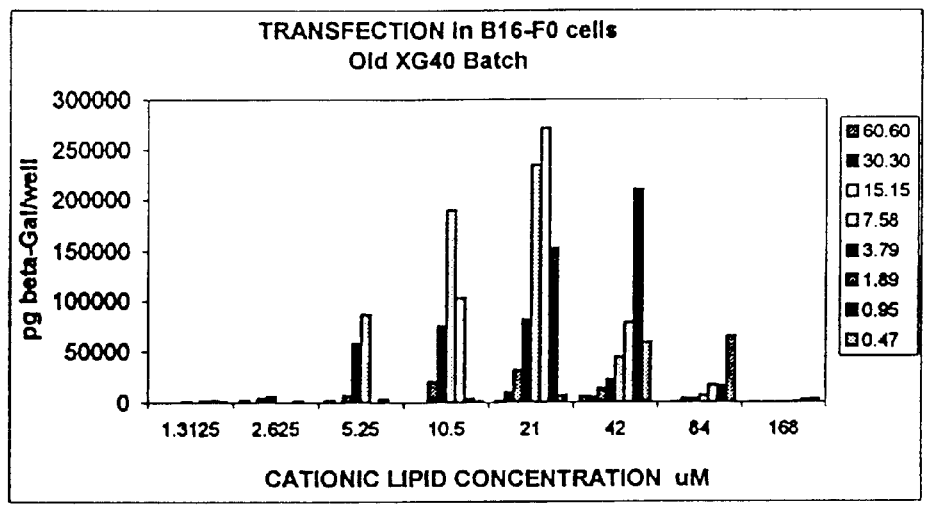
Figure 3B:
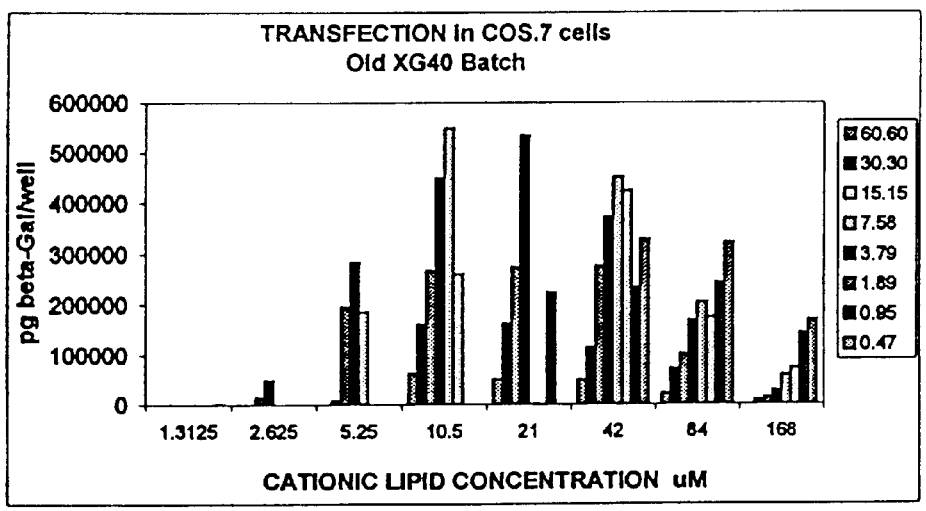
Figure 3C:
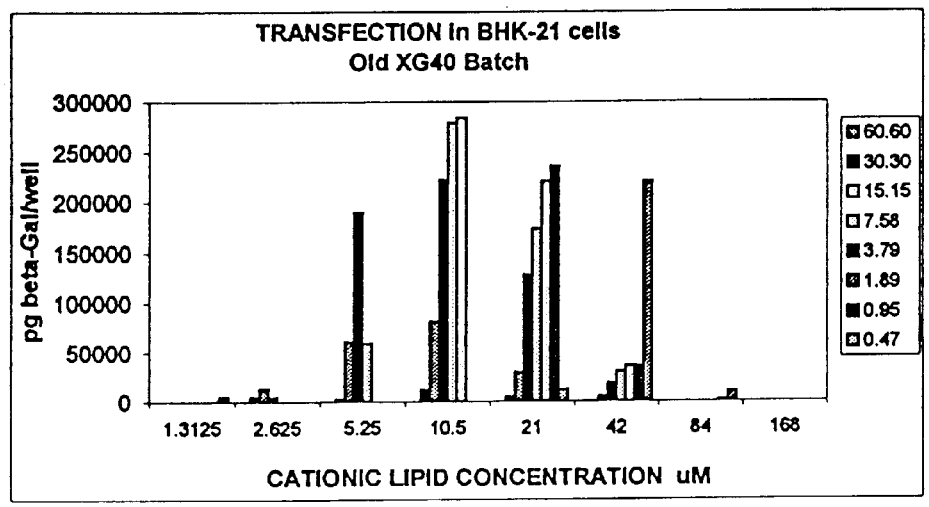
Figure 3D:
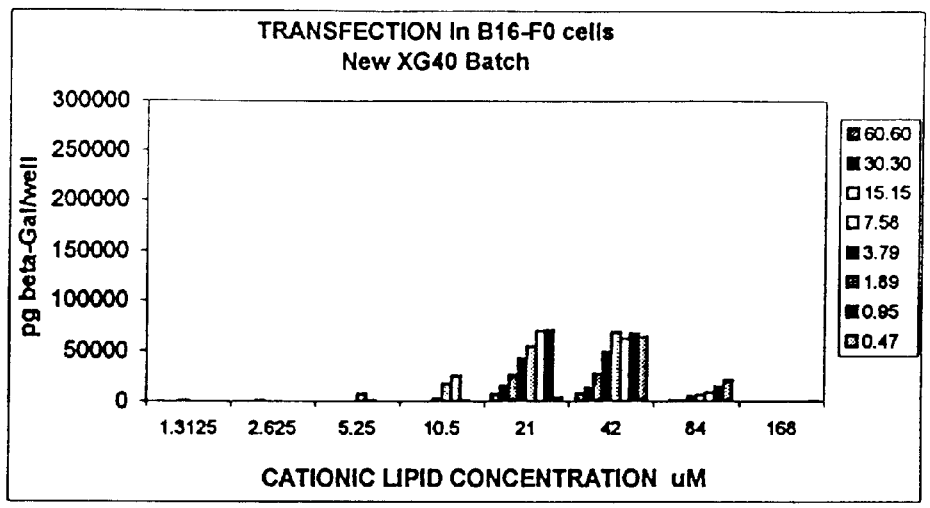
Figure 3E:
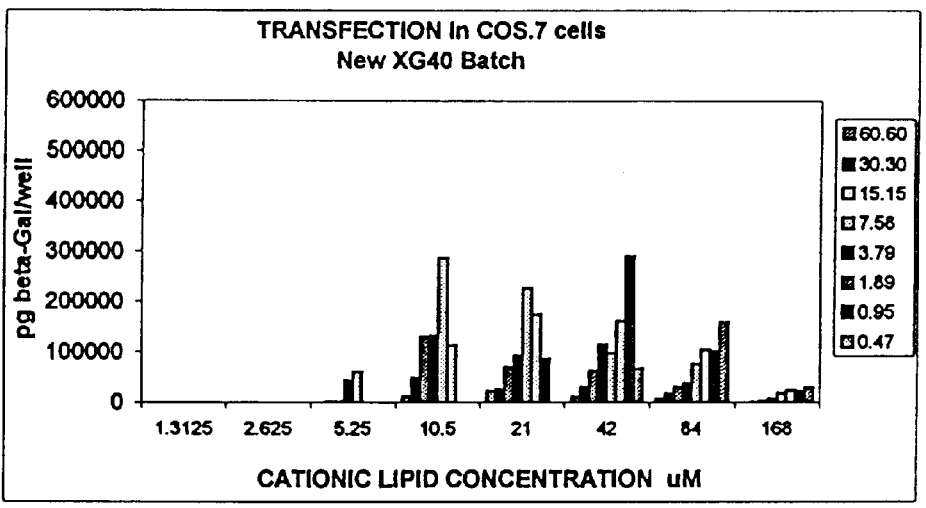
Figure 3F:
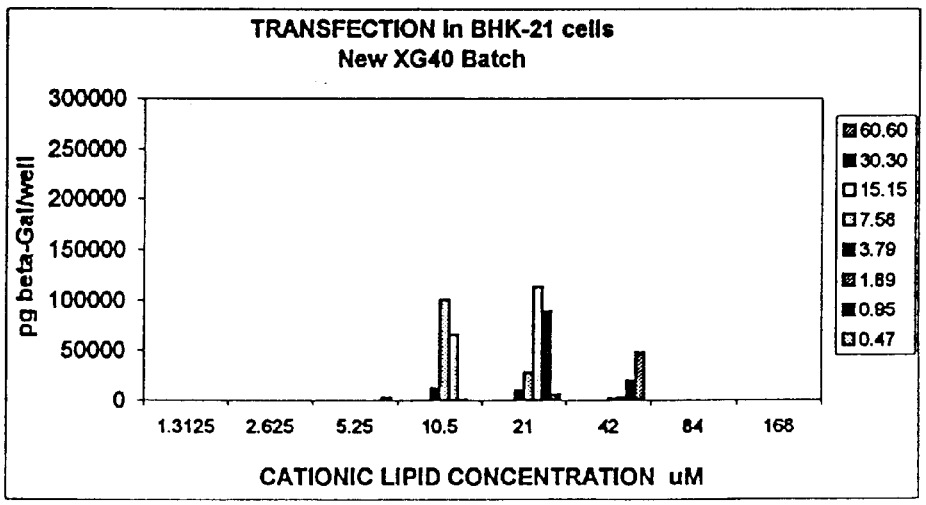

Examples of a preferred lysine-3 species (XG39) is shown in FIG. 1 and a preferred lysine-5 species (XG40) is shown in FIG. 2.

Transfection Formulations

The compounds of the invention can be used to transfect polynucleotides and peptides into cells. Transfection formu-

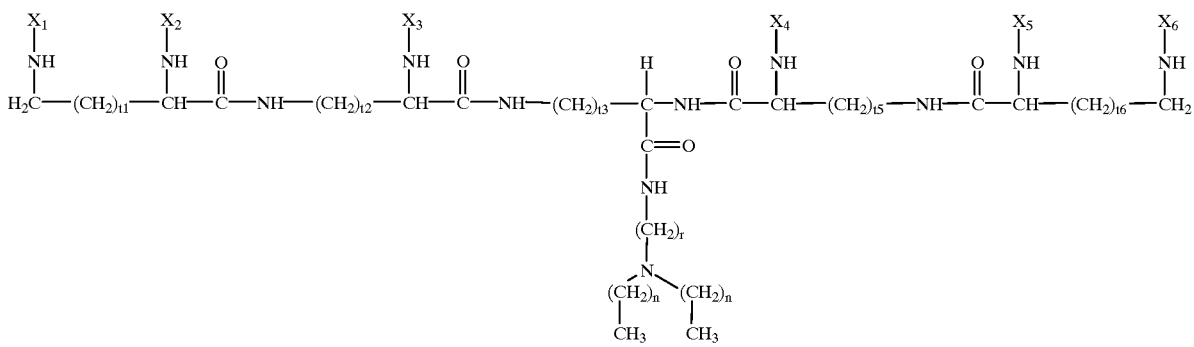

wherein $X_1$, $X_2$, $X_3$, $X_4$, $X_5$ and $X_6$ are independently selected from the group consisting of

H;

tosylate (Tos);

benzyloxycarbonyl (Cbz);

t-butyloxycarbonyl (Boc);

lations comprise novel cationic lipids of the invention having the structure set forth herein, optionally formulated together with an effective, transfection-promoting amount of other neutral colipids. It has been found that improved transfection formulations comprise amphipathic lipids having a polar headgroup and aliphatic components capable of promoting transfection while preserving the ability of the lipid vesicles assembled from the formulation to achieve fusion with cell membranes. Suitable colipids comprise, but are not limited to lysophosphatides, phosphatidylethanolamines, phosphatidylcholines, cholesterol derivatives, fatty acids, mono-, di- and triglyceride phospholipids having a neutral, negative, or positively charged headgroup. Phospholipids having a neutral headgroup are preferred. Other suitable single chain lyso lipids comprise the Rosenthal inhibitor ester and ether derivatives disclosed in U.S. Pat. No. 5,264,618 to Feigner et al. and U.S. Pat. No. 5,459,127 to Felgner et al. which are hereby incorporated by reference.

The cationic lipid formulations alone, or comprising at least one amphipathic lipid, can spontaneously assemble to form primary liposomes, heterogenous in size. Therefore, the lipid reagents of the invention can be prepared as liposomes. Procedures for preparing liposomes for transfection formulations are disclosed and exemplified in the '618 and '127 patents to Felgner et al. cited above. Other procedures for liposome formation are disclosed in Felgner, P. L. et al., Proc Natl Acad Sci USA 84:7413–7417 (1987).

Screening Procedures

These highly potent transfection agents of the invention were discovered while screening 13 novel amphipathic cationic lipids, which were taken from a larger library of 144 compounds. Based on preliminary screening results of transfective ability, one highly active compound, compound XG40, was discovered and selected for further study. A larger batch of the compound was synthesized. Surprisingly a larger synthetic batch of the predicted product "New Batch" was much less active in transfection assays than the original material "Original Batch" when the transfection activities of the two batches were compared in three different cell types (compare FIGS. 3A, 3B and 3C to FIGS. 3D, 3E and 3F, respectively).

Analysis by Mass Spectroscopy

In order to determine the source of this difference the batches were analyzed by mass spectrometry. This analysis showed that the two batches differed chemically (compare FIG. 4A and FIG. 4B). The "New Batch" gave a spectrum showing a molecular ion at 1220, consistent with the calculated molecular weight of the anticipated NG40 compound. However, in the "Original Patch" the 1220 peak was only a minor component and there were a number of molecular ions with higher mass. These higher molecular weight species (peaks 1316, 1412, 1508 were greater than the 1220 peak in multiples of 96. This led us to consider how the original synthesis could have led to a family of compounds that were larger than the anticipated compound by multiples of 96.

Trifluoroacetic acid (TFA) is used in the last step leading to the synthesis of XG40. If TFA had reacted with the primary amino groups in the polar headgroup to form TFA amides the resulting derivatives would be larger than the parent compound by multiples of 96. (The molecular weight of TFA is 114. Amide formation is a dehydration reaction that leads to the removal of water, which has a molecular weight of 18. Thus, 1220+n(114–18)=1220+96n, where n equals the number of TFA amides conjugated to the available primary amines.) This argument suggested that the original batch of XG40 might be a mixture of compounds containing different numbers of trifluoroacetic acid amides conjugated to the primary amino groups in the polar head group, and that the addition of these TFA moieties might be responsible for the improved transfection potency.

In order to test this hypothesis, portions of the new batch were intentionally converted into the TFA conjugated product by reacting the pure XG40 compound with increasing ratios of trifluoroacetic acid and performing mass spectral analysis on the products according to Example 3. The results are shown in FIGS. 5A, 5B and 5C. These studies demonstrated that intentional trifluoroacetylation of the second synthetic batch could convert the composition of the new batch to that of the original product.

The next step was to determine whether the TFA conjugation chemistry could activate transfection activity and restore the potency of the new batch up to the level of the original batch. To that end, the experiment described in Example 4 was carried out. Intentional TFA conjugation of the New XG40 Batch restored the activity of the material up to the level of the Old XG40 Batch in all three of the cell types examined, i.e., B16-F0 (see FIGS. 6A, 6B and 6C), COS-7 (see FIGS. 6D, 6E and 6F) and BHK-21 (see FIGS. 6G, 6H and 6I). The transfection activities of the TFA-conjugated products were compared with the Old XG40 Batch in 8 additional cell types (see all panels of FIG. 7). In HeLa-S3 (see FIGS. 7A, 7B, 7C and 7D), Jurkat (see FIGS. 7E, 7F, 7G and 7H), PC 12 (see FIGS. 7I, 7J, 7K and 7L) and COS.1 cells (see FIGS. 7M, 7N, 7O and 7P), the newly conjugated products (either the T1 or T2 forms) were slightly more active than the Old XG40 Batch. In NIH-3T3 (see FIGS. 7Q, 7R, 7S and 7T), CHO (see FIGS. 7U, 7V, 7W and 7X), 293 (see FIGS. 7Y, 7Z, 7AA and 7BB) and CV1 (see FIGS. 7CC, 7DD, 7EE and 7FF) cells there was no obvious difference in the potency between Old XG40 Batch and the T1 or T2 conjugates. In 8 out of the 11 cell types examined, the activity of the T3 conjugate was depressed relative to the T1 or T2 conjugates. This result indicated that over-conjugation of the XG40 is not beneficial for optimal transfection activity. Overall, these results showed that the TFA conjugation chemistry could restore the transfection potency of pure XG40 up to and beyond the potency of the original batch. The conclusions of these studies are that the T1 and T2 TFA conjugates are equal to or better than the original batch and the T3 TFA conjugates is generally less active than either than the T1 and T2 derivatives.

The compounds derived from this conjugation chemistry have much greater in vitro transfection activity than LipofectAMINE® (compare FIGS. 8A and 8B), which is one of the most active transfection reagents available commercially.

Synthetic Methods

Compounds of formula (I) or (II) can be prepared by adapting the procedure as shown in the Synthesis Scheme wherein a compound comprising a pair of 18:0 fatty acid chains and 3 to 5 lysine groups is prepared (see FIGS. 9 and 10). A dialkyl or dialkenylamine is conjugated to an N-alkylamine, and diprotected lysine groups linked thereto by amide bonds and subsequently deprotected. Specific synthesis of compound XG40 is described in Example 1. Acetate or trifluoroacetate groups are conjugated to the deprotected primary amino groups in the polar headgroup by reacting the purified product of Example 1 with acetic acid or trifluoroacetic acid (Example 2). The extent of conjugation is determined by the molar ratio of the reactants and verified by mass spectral analysis.

Determination of in vitro Transfection Activity

The transfection potency of the compounds of the invention was determined using the following protocol and cell culture systems.

| | |
|---|---|
| Cell Lines | Highly transfected adherent cell line: COS 1 or B16-FO<br>Low transfected adherent cell line: CV-1 or HeLa<br>Suspension cell: Jurkat |
| Culture media | OPTI-MEM ® I (Gibco, BRL) with and without FBS |
| DNA | pCMV-int-LacZ |
| Lipids | Formulated +/− DOPE ® and DMRIE ® (Vical Incorporated, San Diego, CA): DOPE ® was used in each transfection as a reference. Multilamellar liposomes (MLV) were prepared in water. |
| Buffers | 1) Lysis buffer: 250 mM Tris, 0.1% Triton (v/v), pH 8<br>2) 50% glycerol/50% water to resuspend β-gal standard stock (0.8 mg/ml)<br>3) β-galactosidase buffer (1000 ml):<br>60 mM $Na_2HPO_4$, pH 8 (8.52 g)<br>1 mM $MgSO_4$ (120 mg)<br>10 mM KCl (745 mg)<br>50 mM β2-mercaptoethanol (3.5 ml of 14.3M stock solution, d = 1.114 g/ml)<br>4) PBS with 0.5% BSA (PBS 1x without Calcium and Magnesium Salts, Irvine Scientific Cat. #9240) |
| Substrate | CPRG (Boehringer, cat #884308, 250 mg/bottle)<br>β-galactosidase standard purified from *E. coli* (Sigma, cat #G5635, 2 mg/vial). |

1. Lipid Reagent Preparation and Dilution:
    A. Reconstitute each lipid sample and reference vial with sufficient sterile water to make a solution that is 0.672 mM for each lipid in the mixture. Vortex each vial for 1 minute.
    B. Perform two-fold serial dilutions of lipid reagent column-wise on a 96-well, round-bottom plate having 12 columns (designated 1 through 12) and 8 rows (designated A through H).
        (1) Dispense 120 μL of OPTI-MEM® I per well in columns 11 and 12. Dispense 60 μL of OPTI-MEM® per well in columns 1 through 10.
        (2) Dispense 60 μL of 0.672 mM cationic lipid reagent in the wells of column 1 and the well 10A.
        (3) Perform two-fold serial dilutions column-wise from column 1 to column 8 by transferring 60 μl with a multi-channel pipettor.
        (4) Perform two-fold serial dilutions row-wise in column 10 by serially transferring 60 μL from row A to row H. ps 2. DNA Preparation and Dilution:
    A. Prepare a sufficient amount of 0.08 mg/mL solution of pCMV-int-lacZ in OPTI-MEM® I (675 μL is needed per plate).
    B. Perform two-fold serial dilution of DNA on a 96-well, round-bottom plate row-wise.
        (1) Dispense 75 μL of OPTI-MEM® I per well in columns 1 through 10.
        (2) Dispense 75 μL of 0.08mg/ml DNA solution in the wells of row A, 1 through 9.
        (3) Perform two-fold serial dilutions row-wise in column 1 through column 9 from row A to row H by transferring 75 μL with a multi-channel pipettor.
3. Lipid and DNA Complex Formation:
    A. For each well, transfer 60 μL of solution from the DNA dilution plate to the lipid dilution plate at the corresponding well position. Start from column 10 to column 1.
    B. Mix gently by tapping the plate. Use the lipid/DNA mixture for cell transfection between 15 and 60 minutes after complexation.
4. Transfection:
    Remove cell culture medium from 96-well plates containing cells.
    Transfer 100 μL of mixtures on cells.
    Incubate 4 hours at 37° C., 5% $CO_2$ in a humidified incubator.
    Four hours post-transfection, add 50 μL of OPTI-MEM® I (in 30% FBS) per well.

Experimental Procedures

The preparation of the compounds of the present invention is described in detail using the following examples, but the reactions and procedures are disclosed in terms of their general applicability to the preparation and evaluation of the compounds of the invention. Occasionally, the procedure may not be applicable as described to each compound included within the disclosed scope of the invention. The compounds for which this occurs will be readily recognized by those skilled in the art. In all such cases, either the reaction can be successfully performed by conventional modifications known to those skilled in the art, that is, by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily prepared from known starting materials; all temperatures are set forth in degrees Celsius; and unless otherwise indicated, all parts and percentages are by weight.

| Structure Definition |
|---|
| 18-1 |
| $(C_{18}H_{37})_2N(CH_2)_3NH_2$ |
| 18-1-Lys-1 |
| 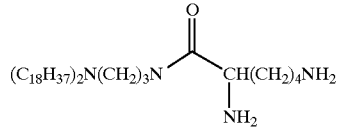 |

-continued
Structure Definition
Arg-(Tos)-18-1
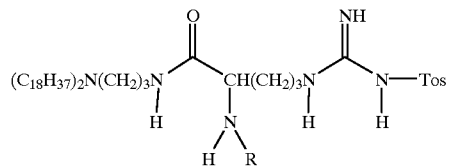
R = H: H-Arg-(Tos)-18-1
R = Boc: Boc-Arg-(Tos)-18-1
Tos:
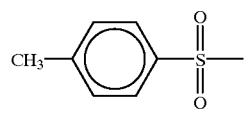
Lys-3-18-1
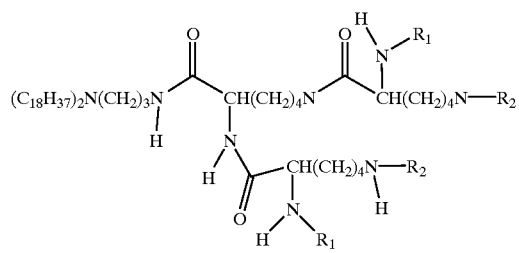
$R_1$ = Boc $R_2$ = H: bis-Boc-Lys-3-18-1
$R_1$ = Cbz $R_2$ = H: bis-ZLys-3-18-1
$R_1$ = CBz $R_2$ = Boc: bis-ZBoc-lysyl lysine amide
Lys-5-18-1
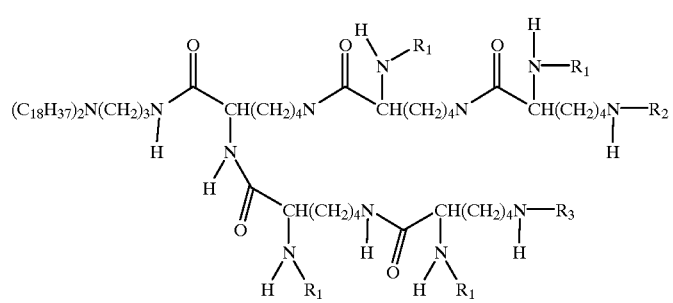
$R_1$ = Boc; $R_2$ = $R_3$ = Tfa: tetrakis-Boc-Lys-5-18-1-Tfa(2)
$R_1$ = Boc; $R_2$ = $R_3$ = Tos: tetrakis-Boc-Lys-5-18-1-Tos(2)
$R_1$ = H; $R_2$ = $R_3$ = Tfa: Lys-5-18-1-Tfa(2)
$R_1$ = H; $R_2$ = $R_3$ = Tos: Lys-5-18-1-Tos(2)
$R_1$ = H; $R_2$ = $R_3$ = Tfa: Lys-5-18-1-Tfa(1)
Tfa = $CF_3C(O)-$

EXAMPLE 1

Synthesis of 18-1-Lys-5 Tε (XG40)

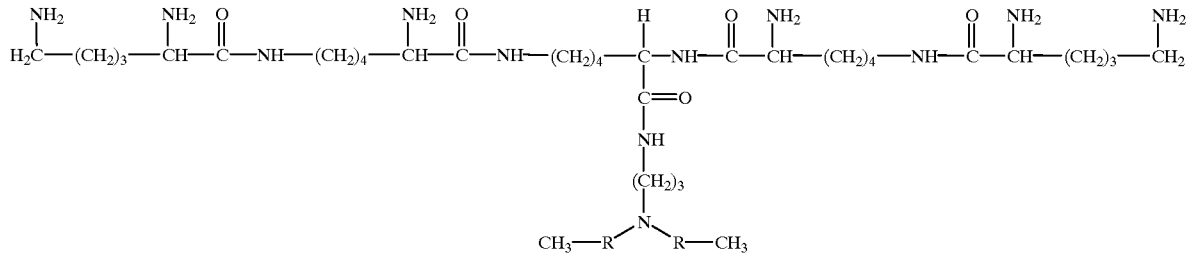

R = 18:1 fatty acid chain

XG40 is synthesized according to the Synthesis Scheme presented in FIG. 10. This scheme leads to the synthesis of 5 grams of product. This synthesis can be carried out twice in order to generate the 10 grams of product required for complete analysis.

Step 1: To a solution containing 10.4 gram (20 mmol) of dioctadecylamine in 100 ml $CH_2Cl_2$: methanol (1:1), 50 ml acrylonitrile is added. The mixture is briefly heated to 60° C. and cooled to room temperature for 12h. The solvent and the excess of acrylonitrile are removed by a rotary evaporator followed by high vacuum. The solid is dissolved in hexane and subjected to normal phase silica gel chromatographic purification. The resulting N-propylnitrile-N-dioctadecylamine is dissolved in 100 ml dioxane and cooled to 4° C. and then reduced to N-propylamine-dioctadecylamine (18-1) using $LiAlH_4$. The excess of $LiAlH_4$ is neutralized with dilute NaOH. The organic phase is filtered, diluted with $CH_2Cl_2$ and washed with water. High yield of 18-1 as white solid is recovered and air dried with $Na_2SO_4$, evaporation of solvents and dried under high vacuum. The resulting 18-1 is used in the next step without further purification.

Step 2: To a solution of 18-1 containing 1:1 ratio of triethylamine (TEA), di-Boc-lysine NHS ester is added at 1:2:1 ratio to the amine. After reaction for 2 h at room temperature, the resulting di-boc-lysine amide of 18-1 will be purified using silica gel. Deprotection of di-boc-lysine amide with $TFA/CH_2Cl_2$ will give rise to 18-1-lys-1. After routine work-up, and removal of solvent, the 18-1-lysine amine will be generated in high yield and will be used in the next reaction without further purification.

Step 3: To a solution of 18-1-lysine-1 in $CH_2Cl_2$ with TEA, α-CBZ-ε-Boc-Lysine, previously activated with dicyclohexylcarbodiimide (DCC) and N-hydroxyl-succinamide (NHS), is added at 2:4:1 ratio to the lysine amide. The reaction is monitored with Ninhydrin reaction[40] until its completion. The resulting bis (Z-Boc-lysyl) lysine amide is purified with silica gel after work-up. The Boc group is removed and bis-Zlys3-18-1 is used for the next reaction.

Step 4: B is Z-boc-lysyl (Bis(Z)lys-3-18-1) and is obtained similar to step 3 and purified by silica gel similar to Z-Boc-lysyl lysine amide. Deprotection of the intermediate with $TFA/CH_2Cl_2$ removes the Boc groups. Further deprotection with $Pd/H_2$ in EtON gives rise to the final product 18-1-lys5Tε. The final product is converted to the chloride salt or methanesulfate salt by an ion exchange method.

EXAMPLE 2

Synthesis of Trifluoroacetylated Derivatives of 18-1-Lys-5 Tε

Randomly trifluoroacetylated derivatives of XG40 are synthesized as follows:

The N-hydroxysuccinamide ester of trifluoroacetic acid was prepared from TFA, N-hydroxysuccinamide and dicyclohexylcarbodiimide (DCC) in dimethylformamide (DMF) in a molar ratio of 1:1.1:1.1, incubated for 20 minutes at room temperature and is then filtered to remove the dicyclohexylurea. One gram of XG40 is dissolved in 10 ml dry methanol and a 10 molar excess of triethylamine (TEA) is added. The activated TFA is added to the XG40 in an appropriate molar ratio to give the desired level of trifluoroacetylation and the mixture is incubated at room temperature for 2 hours. The solvent is evaporated under vacuum, re-dissolved in 5 ml methanol and precipitated with 200 ml ether at −70° C. The precipitate is collected by centrifugation and the process is repeated once. The product is dissolved into 5 ml dry methanol and converted into the methanesulfonic acid (Mes) salt form by reaction with 2 molar excess of Mes to amino (groups. The excess of Mes is removed by repeat ether precipitation. The final product is dried under vacuum as white powder.

EXAMPLE 3

Mass Spectral Analysis of TFA-conjugated Amphiphiles

The electrospray mass spectrometry experiments were performed on a Hewlett-Packard 1100 MSD electrospray mass spectrometer. Electrospray samples were introduced into the analyzer at a rate of 12.0 ml/minute. The positive and negative ions generated by the ion evaporation process entered the analyzer through an interface plate with a 100 micron orifice, while the declustering potential was maintained between 50 and 200V to control the collisional energy of the entering ions.

Portions of a batch of synthesized amphiphiles were intentionally converted into the TFA-conjugated product by reacting the pure XG40 compound with increasing concentrations of TFA. The mass spectral analyses shown in FIGS. 5A, 5B and 5C revealed that the products of these syntheses were similar to the material that was present in the original batch (FIG. 4B). As the amount of TFA in the reaction was increased, the 1220 molecular weight ion was progressively reduced and families of compounds with molecular weights of 1220+96n were generated. The molecular ion distribution pattern obtained when either 1 or 2 moles of TFA was reacted per mole of XG40 (FIG. 5A, 5B), looked similar to the pattern obtained in the original batch. When 3 moles of TFA were reacted per mole of XG40 (FIG. 5C), the distribution of the TFA conjugates was shifted to a significantly higher molecular weight pattern than was obtained in the original batch. The product shown in FIG. 5C was a mixture of five species with molecular weights of 1220, 1316, 1412, 1508 and 1604 corresponding to 0, 1, 2, 3 or 4 TFA amides conjugated to the available 6 primary amino groups in the polar head group.

EXAMPLE 4

In Vitro Transfection Activity of TFA-conjugated Lysine-3 and Lysine-5 Amphiphile Derivatives A set of 13 cationic amphiphiles were synthesized and screened for in vitro transfection activity using the sensitive, quantitative in vitro assay described above that was developed in our laboratory. In B16 mouse melanoma cells, the lysine-3 (XG39) and lysine-5 old (XG40) derivatives were found to be the most active. XG39 and XG40 were further compared in two different cell types. Old XG40 was more active in COS 7 cells, and considerably more active in BHK-21 cells.

The transfection activity of old XG40 in BHK-21 cells was compared with LipofectAMINE®. LipofectAMINE® was selected for this comparison because it is one of the most potent commercially available transfection reagents. The data in FIGS. 8A and 8B show that old XG40 was considerably more active than LipofectAMINE®. This result indicates that old XG40 may be the most active transfection reagent of its kind yet described.

EXAMPLE 5

Synthesis of H-Arg(Tos)-18-1.HCl

To a 100 mL round-bottomed flask containing a solution of 18-1 (579 mg, 1 mmol, prepared as described in Example 1, step 1) in 10 mL $CH_2Cl_2$, were added Boc-Arg(Tos)-OH (428.5 mg, 1 mmol), 1-Hydroxybenzotriazole Hydrate (HOBt, 135.1 mg, 1 mmol) and N-(3-Dimethylaminopropyl)-N'-ethylcarbodiimide hydrochloride (EDC, 191.7 mg, 1 mmol), respectively. The resulting mixture was stirred at room temperature for several hours. When no more 18-1 was detected by Thin Layer Chromatography (TLC), the reaction was stopped. After flash chromatography over silica gel, Boc-Arg(Tos)-18-1 was obtained as a colorless solid. The Boc-Arg(Tos)-18-1 thus obtained was then submitted to the treatment of HCl/ether at room temperature for an hour. The reaction mixture was concentrated to dryness under rotary evaporation to afford the title compound as a HCl salt.

EXAMPLE 6

Assay Results of H-Arg(Tos)-18-1.HCl

Assay results from evaluation of H-Arg(Tos)-18-1 HCl (in NIH-3T3 and HeLa-S3 cells) are presented in FIGS. 11A–11D.

EXAMPLE 7

Synthesis of a di-trifluoroacetylated Derivative of XG40 [lys-5-18-1-Tfa(2)]

Similar to the preparation of bis-Z-lys-3-18-1 as described in Example 1, step 3, bis-Boc-lys-3-18-1 was prepared from the reaction of 18-1-lysine-1 with 2 equivalents of Boc-lys (Z)-OH in the presence of DCC and NHS as activating agents and the Z group of the coupling reaction product was removed under hydrogenation condition using Pd/C catalyst. The bis-Boc-lys-3-18-1 thus produced reacted with 2 equivalents of Boc-lys(Tfa)-NHS at room temperature in $CH_2Cl_2$ to afford tetrakis-Boc-lys-5-1-1-Tfa(2), which was purified by flash chromatography over silica gel. The Boc groups of the tetrakis-Boc-lys-5-18-1-Tfa(2) were removed by methanesulfonic acid/$CH_2Cl_2$. The resulting lys-5-18-1-Tfa(2).Mes salt was washed 3 times with ether at room temperature, dried under vacuum and obtained as a white solid.

EXAMPLE 8

Assay Results of [lys-5-18-1-Tfa(2)]

Assay results for evaluation of [lys-5-18-1-Tfa(2)] (in NIH-3T3 and HeLa-S3 cells) are presented in FIGS. 12A–12D.

EXAMPLE 9

Synthesis of a Mixture of a Mono- and Di-trifluoroacetylated Derivative of XG40 [lys-5-18-1-Tfa(1)]+[lys-5-18-1-Tfa(2)]

Tetrakis-Boc-lys-5-18-1-Tfa(2) (prepared as described in EXAMPLE 7) was treated by methansulfonic acid in methanol at room temperature for 14 hours and the mass spectra showed the reaction product was a mixture of lys-5-18-1-Tfa(1)+lys-5-18-1-Tfa(2). The mixture was washed 3 times with ether at room temperature, dried under vacuum and obtained as a white solid in the form of Mes salts.

EXAMPLE 10

Assay Results of [lys-5-18-1-Tfa(1)]+[lys-5-18-1-Tfa(2)]

Assay results for evaluation of a mixture of [lys-5-18-1-Tfa(1)] and [lys-5-18-1-Tfa(2)] (in NIH-3T3 and HeLa-S3 cells) are presented in FIGS. 13A–13D.

EXAMPLE 11

Synthesis of a Di-tosylated Derivative of XG40 [lys-5-18-1-Tos(2)]

One equivalent of 18-1-lysine-1 reacted with 2 equivalents of Boc-lys(Z)-OH in the presence of DCC and NHS as activating agents to form a coupling reaction product. The Z group of the coupling reaction product was removed under hydrogenation condition using Pd/C catalyst. The bis-Boc-lys-3-18-1 thus produced reacted with 2 equivalents of Boc-lys(Tos)-NHS at room temperature in $CH_2Cl_2$ to afford tetrakis-Boc-lys-5-18-1-Tos(2), which was purified by flash chromatography over silica gel. The Boc groups of the tetrakis-Boc-lys-5-18-1-Tos(2) were removed by methanesulfonic acid/$CH_2Cl_2$. The resulting lys-5-18-1-Tos(2).Mes salt was washed 3 times with ether at room temperature, dried under vacuum and obtained as a white solid.

EXAMPLE 12

Assay Results of [lys-5-18-1-Tos(2)]

Assay results for evaluation of [lys-5-18-1-Tos(2)] (in NIH-3T3 and HeLa-S3 cells) are presented in FIGS. 14A–14D.

EXAMPLE 13

Synthesis of Acetylated Derivatives of XG40 [XG40-A1]+[XG40-A2]

The synthesis of acetylated derivatives of XG40 is identical with that of trifluoroacetylated derivatives of XG40 as described in EXAMPLE 2 except that acetic acid is substituted for trifluoroacetic acid. XG40-A1 and XG40-A2 refer to the products respectively when one and two equivalents of activated acetic acid are used.

EXAMPLE 14

Assay Results of [XG40-A1]+[XG40-A2]

Assay results for evaluation of a mixture of [XG40-A1] and [XG40-A2] (in Jurkat and NIH-3T3 cells) are presented in FIGS. 15A–15F.

References

1. Wolff, J. A. et al. Direct gene transfer into mouse muscle in vivo. *Science* 247, 1465–1468 (1990).
2. Ulmer, J. B. et al. Heterologous protection against influenza by injection of DNA encoding a viral protein [see comments]. *Science* 259, 1745–1749 (1993).
3. Behr, J. P. Gene transfer with synthetic cationic amphiphiles: prospects for gene therapy. *Bioconjug. Chem.* 5, 382–389 (1994).
4. Gao, X. and Huang, L. Cationic liposome-mediated gene transfer. *Gene Therapy* 2, 710–722 (1995).
5. Donnelly, J. J. et al. DNA vaccines. *Ann. Rev. Immunol.* 15, 617–648 (1997).
6. Felgner, P. L. Nonviral strategies for gene therapy. *Sci. Am.* 276, 102–106 (1997).
7. Felgner, P. L. DNA vaccines. *Current Biol.* 8, 551–553 (1998).
8. Mahato, R. I. et al. Cationic lipid-based gene delivery systems: pharmaceutical perspectives. *Pharm. Res.* 14, 853–859 (1997).
9. Felgner, P. L. Improvements in cationic liposomes for in vivo gene transfer [editorial]. *Hum. Gene Ther.* 7, 1791–1793 (1996). for use in gene therapy. *Gene Therapy* 3, 350–356 (1996).
10. Hartikka, J. et al. An improved plasmid DNA expression vector for direct injection into skeletal muscle. *Hum. Gene Ther.* 7, 1205–1217 (1996).
11. Liang, X. et al. Novel, high expressing and antibiotic-controlled plasmid vectors designed for use in gene therapy. *Gene Therapy* 3 350–356 (1996).
12. Cooper, M. J. et al. Safety-modified episomal vectors for human gene therapy. *Proc. Natl. Acad. Sci. USA* 94, 6450–6455 (1997).
13. Roman, M. et al. Immunostimulatory DNA sequences function as T helper-1-promoting adjuvants. *Nature Medicine* 3, 849–854 (1997).
14. Gao, X. and Huang, L. A novel cationic liposome reagent for efficient transfection of mammalian cells. *Biochem. Biophys. Res. Commun.* 179, 280–285 (1991).
15. Felgner, P. L. and Rhodes, G. Gene therapeutics. *Nature* 349, 351–352 (1991).
16. Gao, X. and Huang, L. Cytoplasmic expression of a reporter gene by co-delivery of T7 RNA polymerase and T7 promoter sequence with cationic liposomes. *Nucleic Acids Res.* 21, 2867–2872 (1993).
17. Gao, X. and Huang, L. Potentiation of cationic liposome-mediated gene delivery by polycations. *Biochemistry* 35, 1027–1036 (1996).
18. Caplen, N. J. et al. Liposome-mediated CFTR gene transfer to the nasal epithelium of patients with cystic fibrosis [published erratum appears in Nature Med. March 1995; 1(3):272]. *Nature Med.* 1, 39–46 (1995).

What is claimed is:

1. A method for introducing a biologically active agent into a cell of a plant or animal, said method comprising contacting said cell with lipid vesicles containing said biologically active agent, said lipid vesicles comprising an amphiphilic polyamide having the structure:

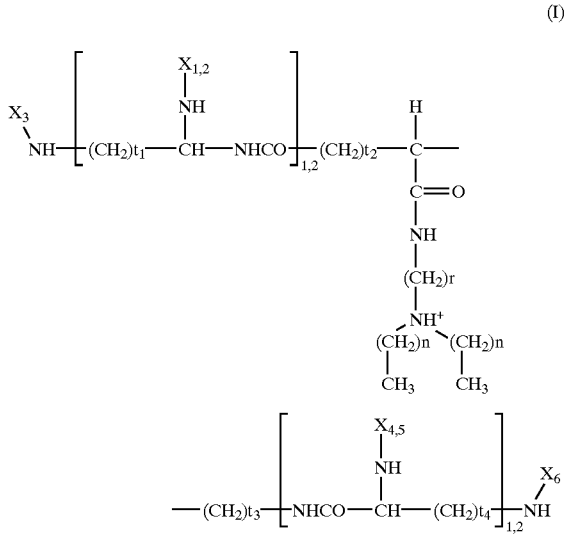

wherein:

each of $X_1$, $X_2$, $X_3$, $X_4$, $X_5$ and $X_6$ is independently selected from the group consisting of amino-protecting groups comprising a carboxyl group or a sulfonyl group and capable of forming an amide bond;

r is an integer from 0 to 5;

n is an integer from 7 to 21; and each of $t_1$, $t_2$, $t_3$ and $t_4$ is independently an integer from 0 to 5, whereby said biologically active agent is taken up into said cell.

2. The method according to claim 1, wherein said biologically active agent is a polynucleotide.

3. The method according to claim 2, wherein said polynucleotide is DNA or mRNA coding for a polypeptide, wherein said polypeptide is expressed after said DNA or said mRNA is taken up into said cell.

4. The method according to claim 2, wherein said polynucleotide is an oligonucleotide.

5. The method according to claim 4, wherein said oligonucleotide is DNA or mRNA.

6. The method according to claim 1, wherein said biologically active agent is a polypeptide.

7. The method according to claim 1, wherein said contacting step occurs in vitro.

8. The method according to claim 1, wherein said contacting step occurs in vivo.

9. The method according to claim 1, wherein $X_1$, $X_2$, $X_3$, $X_4$, $X_5$ and $X_6$ of said amphiphilic polyamide is each independently selected from the group consisting of H, tosylate (Tos), benzyloxycarbonyl (Cbz), t-butyloxycarbonyl (Boc), $H_3C-C(O)-$, and $F_3C-C(O)-$, and wherein:

r is an integer from 1 to 4;

n is an integer from 7 to 21; and each of $t_1$, $t_2$, $t_3$ and $t_4$ is independently an integer from 0 to 5.

10. The method according to claim 9, wherein $X_1$, $X_2$, $X_3$, $X_4$, $X_5$ and $X_6$ of said amphiphilic polyamide is each independently selected from the group consisting of H, tosylate (Tos), benzyloxycarbonyl (Cbz), t-butyloxycarbonyl (Boc), $H_3C$—C(O)—, and $F_3C$—C(O)—, and wherein:

r is 3, n is 17; and each of $t_1$, $t_2$, $t_3$ and $t_4$ is 4.

11. A method for introducing a biologically active agent into a cell of a plant or animal, said method comprising contacting said cell with a biologically active agent in the presence of lipid vesicles comprising an amphiphilic polyamide having the structure:

(II)

$$X_1\text{NH}-H_2C-(CH_2)_{t_1}-CH(X_2\text{NH})-C(O)NH-(CH_2)_{t_2}-CH(X_3\text{NH})-C(O)NH-(CH_2)_{t_3}-C(\text{NHC}(O)...)(X_4\text{NH})-CH-(CH_2)_{t_5}-NHC(O)-CH(X_5\text{NH})-(CH_2)_{t_6}-CH_2(X_6\text{NH})$$

with side chain: C=O—NH—$(CH_2)_r$—N($(CH_2)_n CH_3$)($(CH_2)_n CH_3$)

wherein:

each of $X_1$, $X_2$, $X_3$, $X_4$, $X_5$ and $X_6$ is independently selected from the group consisting of amino-protecting groups comprising a carboxyl group or a sulfonyl group and capable of forming an amide bond;

r is an integer from 0 to 5;

n is an integer from 7 to 21; and each of $t_1$, $t_2$, $t_3$, $t_5$ and $t_6$ is independently an integer from 0 to 5, and whereby said biologically active agent is taken up into said cell.

12. The method according to claim 11, wherein $X_1$, $X_2$, $X_3$, $X_4$, $X_5$ and $X_6$ of said amphiphilic polyamide is each independently selected from the group consisting of H, tosylate (Tos), benzyloxycarbonyl (Cbz), t-butyloxycarbonyl (Boc), $H_3C$—C(O)—, and $F_3C$—C(O)—, and wherein:

r is an integer from 1 to 4;

n is an integer from 9 to 19; and each of $t_1$, $t_2$, $t_3$, $t_5$ and $t_6$ is independently an integer from 0 to 5.

13. The method according to claim 12, wherein $X_1$, $X_2$, $X_3$, $X_4$, $X_5$ a nd $X_6$ of said amphiphilic polyamide is each independently selected from the group consisting of H, tosylate (Tos), benzyloxycarbonyl (Cbz), t-butyloxycarbonyl (Boc), $H_3C$—C(O)—, and $F_3C$—C(O)—, and wherein:

r is 3, n is 17; and each of $t_1$, $t_2$, $t_3$, $t_5$ and $t_6$ is 4.

14. The method according to claim 13, wherein each of $X_1$, $X_2$, $X_3$, $X_4$, $X_5$ and $X_6$ are hydrogen.

15. The method according to claim 13, wherein:

$X_1$ and $X_6$ are $CF_3$—C(O)—, and $X_2$, $X_3$, $X_4$ and $X_5$ are —H.

16. The method according to claim 13, wherein:

$X_1$ and $X_6$ are tosylate, and $X_2$, $X_3$, $X_4$ and $X_5$ are —H.

17. The method according to claim 11, wherein said biologically active agent is a polynucleotide.

18. The method according to claim 17, wherein said polynucleotide is DNA or mRNA coding for a polypeptide, wherein said polypeptide is expressed after said DNA or said mRNA is taken up into said cell.

19. The method according to claim 17, wherein said polynucleotide is an oligonucleotide.

20. The method according to claim 19, wherein said oligonucleotide is DNA or mRNA.

21. The method according to claim 11, wherein said biologically active agent is a polypeptide.

22. The method according to claim 11, wherein said contacting step occurs in vitro.

23. The method according to claim 11, wherein said contacting step occurs in vivo.

24. A method of treating a disease in a vertebrate, said method comprising: administering a pharmaceutical formulation comprising a therapeutically effective amount of a biologically active agent specific for the treatment of said disease, and an amphiphilic polyamide having the structure:

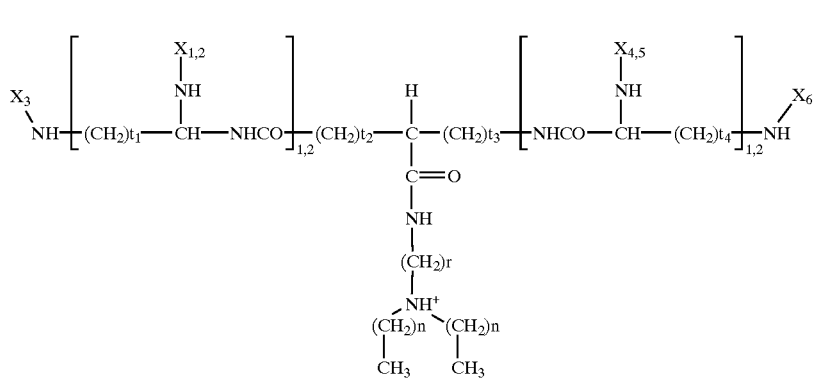

(I)

wherein:

each of $X_1$, $X_2$, $X_3$, $X_4$, $X_5$ and $X_6$ is independently selected from the group consisting of amino-protecting groups comprising a carboxyl group or a sulfonyl group and capable of forming an amide bond;

r is an integer from 0 to 5;

n is an integer from 7 to 21; and each of $t_1$, $t_2$, $t_3$ and $t_4$ is independently an integer from 0 to 5, and permitting said biologically active agent to be incorporated into at least one cell of said vertebrate, whereby said disease is effectively treated.

25. The method according to claim 24, wherein said pharmaceutical formulation is administered to said cells of said vertebrate in vitro, whereby said cells are then returned to said vertebrate.

26. The method according to claim 24, wherein said formulation is applied topically to the skin or mucosal surface.

27. The method according to claim 24, wherein said formulation is injected into a body cavity or tissue of said vertebrate.

28. The method according to claim 24, wherein said formulation is administered orally.

29. The method according to claim 24, wherein said biologically active agent is a polynucleotide.

30. The method according to claim 29, wherein said polynucleotide is DNA or mRNA coding for a polypeptide, and said polypeptide is expressed after said DNA or said mRNA is taken up into said cell.

31. The method according to claim 29, wherein said polynucleotide is an oligonucleotide.

32. The method according to claim 31, wherein said oligonucleotide is DNA or mRNA.

33. The method according to claim 24, wherein said biologically active agent is a polypeptide.

34. The method according to claim 24, wherein said biologically active agent is a drug.

35. A method of generating antibodies to an immunogen in a mammal, said method comprising directly administering to mammalian tissue a DNA sequence encoding said immunogen operatively linked to a promoter or a mRNA sequence encoding said immunogen, wherein said sequence is complexed to an amphiphilic polyamide having the structure:

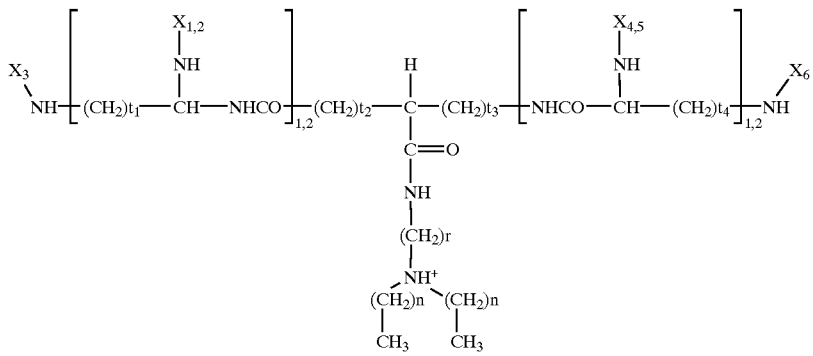

wherein:

each of $X_1$, $X_2$, $X_3$, $X_4$, $X_5$ and $X_6$ is independently selected from the group consisting of amino-protecting groups comprising a carboxyl group or a sulfonyl group and capable of forming an amide bond;

r is an integer from 0 to 5;

n is an integer from 7 to 21; and each of $t_1$, $t_2$, $t_3$ and $t_4$ is independently an integer from 0 to 5, in an amount sufficient to induce detectable production of desired antibodies to the expressed immunogen.

36. The method according to claim 35, wherein $X_1$, $X_2$, $X_3$, $X_4$, $X_5$ and $X_6$ of said amphiphilic polyamide is each independently selected from the group consisting of H, tosylate (Tos), benzyloxycarbonyl (Cbz), t-butyloxycarbonyl (Boc), H$_3$C—C(O)—, and F$_3$C—C(O)—, and wherein:

r is an integer from 1 to 4;

n is an integer from 9 to 19; and each of $t_1$, $t_2$, $t_3$ and $t_4$ is independently an integer front 0 to 5.

37. The method according to claim 36, wherein $X_1$, $X_2$, $X_3$, $X_4$, $X_5$ and $X_6$ of said amphiphilic polyamide is each independently selected from the group consisting of H, tosylate (Tos), benzyloxycarbonyl (Cbz), t-butyloxycarbonyl (Boc), H$_3$C—C(O)—and F$_3$C—C(O)—, and wherein:

r is 3, n is 17; and each of $t_1$, $t_2$, $t_3$ and $t_4$ is 4.

38. The method according to claim 35, wherein administration is accomplished by injection.

39. The method according to claim 38, wherein said injection is inoculation through a needle.

40. The method of claim 35, wherein said tissue is muscle.

41. The method of claim 35, wherein said tissue is skin.

42. The method of claim 35, wherein said tissue is mucous membrane.

43. The method of claim 35, wherein said mammal is human.

44. The method of claim 35, wherein a DNA sequence encodes said immunogen.

45. The method of claim 44, wherein said DNA sequence is plasmid.

46. A compound having the following structure:

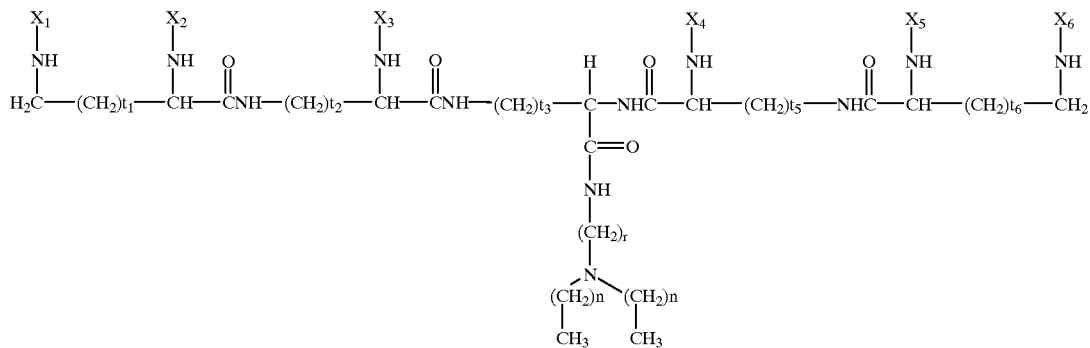

(II)

wherein:

each of $X_1$, $X_2$, $X_3$, $X_4$, $X_5$ and $X_6$ is independently selected from the group consisting of amino-protecting groups comprising a carboxyl group or a sulfonyl group and capable of forming an amide bond;

r is an integer from 0 to 5;

n is an integer from 7 to 21; and each of $t_1$, $t_2$, $t_3$, $t_5$ and $t_6$ is independently an integer from 0 to 5.

47. A compound according to claim 46, wherein each of $X_1$, $X_2$, $X_3$, $X_4$, $X_5$ and $X_6$ are hydrogen.

48. A compound according to claim 46, wherein:

$X_1$ and $X_6$ are CF$_3$—C(O)—, and $X_2$, $X_3$, $X_4$ and $X_5$ are —H.

49. A compound according to claim 46, wherein:

$X_1$ and $X_6$ are tosylate, and $X_2$, $X_3$, $X_4$ and $X_5$ are —H.

* * * * *